US011167046B2

(12) United States Patent
Draney et al.

(10) Patent No.: US 11,167,046 B2
(45) Date of Patent: Nov. 9, 2021

(54) IR DYES FOR FLUORESCENCE IMAGING

(71) Applicant: LI-COR, INC., Lincoln, NE (US)

(72) Inventors: Daniel R. Draney, Lincoln, NE (US); William M. Volcheck, Lincoln, NE (US); Katie Schaepe, Lincoln, NE (US); Vassil Elitzin, Lincoln, NE (US); Joy Kovar, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 69 days.

(21) Appl. No.: 16/687,450

(22) Filed: Nov. 18, 2019

(65) Prior Publication Data

US 2020/0085976 A1 Mar. 19, 2020

Related U.S. Application Data

(63) Continuation of application No. 14/949,654, filed on Nov. 23, 2015, now Pat. No. 10,548,991.

(60) Provisional application No. 62/084,971, filed on Nov. 26, 2014.

(51) Int. Cl.
*A61K 49/00* (2006.01)
*C09B 23/10* (2006.01)
*A61B 5/00* (2006.01)
*A61B 5/20* (2006.01)
*C09B 23/01* (2006.01)
*C09B 23/08* (2006.01)

(52) U.S. Cl.
CPC ........ *A61K 49/0032* (2013.01); *A61B 5/0071* (2013.01); *A61B 5/0084* (2013.01); *A61B 5/20* (2013.01); *A61B 5/4244* (2013.01); *C09B 23/0025* (2013.01); *C09B 23/0066* (2013.01); *C09B 23/086* (2013.01); *C09B 23/107* (2013.01)

(58) Field of Classification Search
None
See application file for complete search history.

(56) References Cited

U.S. PATENT DOCUMENTS

| | | | |
|---|---|---|---|
| 7,488,468 B1 | 2/2009 | Miwa et al. | |
| 7,597,878 B2 | 10/2009 | Kovar et al. | |
| 7,993,927 B2 | 8/2011 | Frangioni | |
| 10,100,198 B2 | 10/2018 | Kundu et al. | |
| 2008/0154102 A1 | 6/2008 | Frangioni et al. | |
| 2011/0280806 A1 | 11/2011 | Nairne et al. | |
| 2016/0144058 A1 | 5/2016 | Draney et al. | |
| 2018/0296704 A1 | 10/2018 | Elitzin et al. | |

FOREIGN PATENT DOCUMENTS

| | | | |
|---|---|---|---|
| EP | 753584 A1 | 1/1997 | |
| JP | 06145539 A | 5/1994 | |
| WO | 0016810 A1 | 3/2000 | |
| WO | 2008076467 A2 | 6/2008 | |
| WO | 2010091243 A1 | 8/2010 | |
| WO | 2016085884 A1 | 6/2016 | |

OTHER PUBLICATIONS

U.S. Appl. No. 16/687,479, filed Nov. 18, 2019, Draney.
Akers et al., "Predicting in Vivo Fluorescence Lifetime Behavior of Near-infrared Fluorescent Contrast Agents using in Vitro Measurements," Journal of Biomedical Optics, vol. 13, No. 5, Sep./Oct. 2008, pp. 054042-1-054042-9.
Caira, "Crystalline Polymorphism of Organic Compounds," Topics In Current Chemistry, Springer, vol. 198, Jan. 1, 1998, pp. 163-208.
Goiffon et al., "Dynamic Noninvasive Monitoring of Renal Function in Vivo by Fluorescence Lifetime Imaging," Journal of Biomedical Optics, vol. 14, No. 2, 2009, pp. 020501-1-020501-3.
PCT/US2015/062212, "International Search Report and Written Opinion," dated May 3, 2016, 17 pages.
Sato et al., "Role of Fluorophore Charge on the in Vivo Optical Imaging Properties of Near-Infrared Cyanine Dye/Monoclonal Antibody Conjugates," Bioconjugate Chemistry, ACS Publications, Oct. 2015, pp. 1-48.
Schols et al., "Application of a New Dye for Near-Infrared Fluorescence Laparoscopy of the Ureters: Demonstration in a Pig Model," Diseases of the Colon & Rectum, vol. 57, Mar. 2014, pp. 407-411.
Schols , "Near-Infrared Fluorescence Laparoscopy of the Cystic Duct and Artery in Pigs: Performance of a Preclinical Dye," Journal of Laparoendoscopic & Advanced Surgical Techniques, vol. 24, No. 5, Nov. 2014, pp. 318-323.
Tanaka et al., "Real-Time Intraoperative Ureteral Guidance Using Invisible Near-Infrared Fluorescence," Journal of Urology, vol. 178, No. 5, Nov. 2007, pp. 2197-2202.
Zaheer et al., "IRDYE78 Conjugates for near-infrared Fluorescence Imaging," Molecular Imaging, vol. 1, No. 4, Oct. 1, 2002, pp. 354-364.
U.S. Appl. No. 15/951,911, "Non-Final Office Action," dated Sep. 10, 2019, 17 pages.
JP2017-527921, "Office Action," dated Jul. 23, 2019, 10 pages.
TW104139216, "Office Action," dated Dec. 19, 2019, 14 pages.

(Continued)

*Primary Examiner* — Jennifer Lamberski
(74) *Attorney, Agent, or Firm* — Kilpatrick Townsend & Stockton LLP

(57) ABSTRACT

A method for organ imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate or 2-((E)-2-((E)-3-(2-((E)-3,3-dimethyl-5-sulfonato-1-(4-sulfonatobutyl)indolin-2-ylidene) ethylidene)-2-(4-sulfonatophenoxy)cyclohex-1-en-1-yl) vinyl)-3,3-dimethyl-1-(4-sulfonatobutyl)-3H-indol-1-ium-5-sulfonate. In one embodiment, the organ includes one or more of kidney, bladder, liver, gall bladder, spleen, intestine, heart, lungs and muscle.

17 Claims, 24 Drawing Sheets

(56) References Cited

OTHER PUBLICATIONS

U.S. Appl. No. 14/949,654, "Supplemental Notice of Allowability," dated Oct. 22, 2019, 2 pages.
PCT/US2018/026882, "International Search Report and Written Opinion," dated Aug. 31, 2018, 20 pages.
PCT/US2018/026882, "International Preliminary Report on Patentability," dated Oct. 24, 2019, 13 pages.
Bilimoria et al., "Laparoscopic-assisted vs. open colectomy for cancer: comparison of short-term outcomes from 121 hospitals," J Gastrointest Surg, (2008), vol. 12, No. 11, pp. 2001-2009.
Kobayashi et al., "Total laparoscopic hysterectomy in 1253 patients using an early ureteral identification technique," J Obstet Gynaecol Res, (2012), vol. 38, No. 9, pp. 1194-1200.
Park et al., "Ureteral injury in gynecologic surgery: a 5-year review in a community hospital," Korean J. Urol., (2012), vol. 53, No. 2, pp. 120-125.
Simorov et al., "Laparoscopic colon resection trends in utilization and rate of conversion to open procedure: a national database review of academic medical centers," Ann Surg., (2012), vol. 256, No. 3, pp. 462-468.
U.S. Appl. No. 14/949,654, "Advisory Action," dated Jan. 22, 2019, 4 pages.
U.S. Appl. No. 14/949,654, "Final Office Action," dated Nov. 19, 2018, 10 pages.
U.S. Appl. No. 14/949,654, "Non-Final Office Action," dated Apr. 5, 2018, 9 pages.
AR20150103806, "Office Action," dated Jan. 10, 2020, 5 pages.
CN201580064045.8, "Office Action," dated Dec. 26, 2019, 23 pages.
JP2017-527921, "Notice of Decision To Grant," dated Feb. 4, 2020, 1 page.
Kumar et al., "An Overview of Automated Systems Relevant in Pharmaceutical Salt Screening," Drug Discovery Today, vol. 12, Nos. 23/24, Dec. 2007, pp. 1046-1053.
Tanaka et al., "Real-Time Intraoperative Ureteral Guidance Using Invisible Near-Infrared Fluorescence", Journal of Urology, vol. 178, No. 5, Oct. 2007, pp. 2197-2202.
U.S. Appl. No. 16/687,479, Non-Final Office Action, dated Apr. 1, 2021, 13 pages.

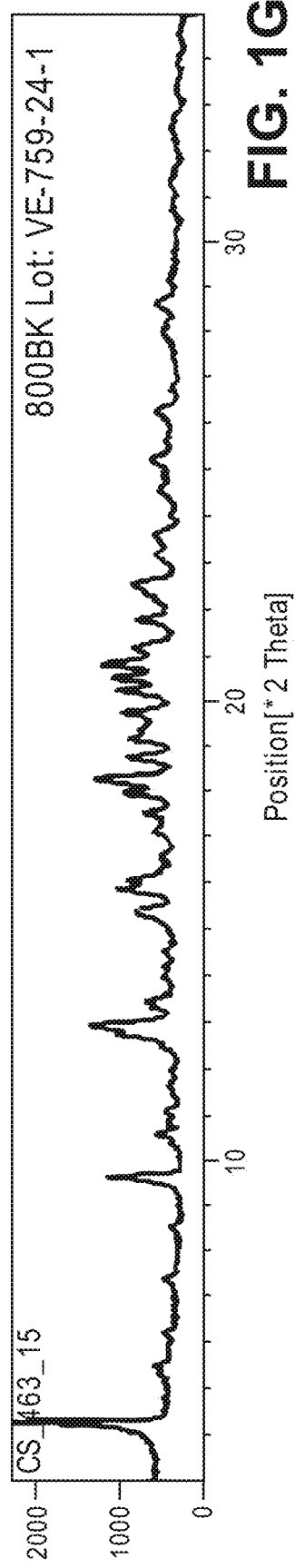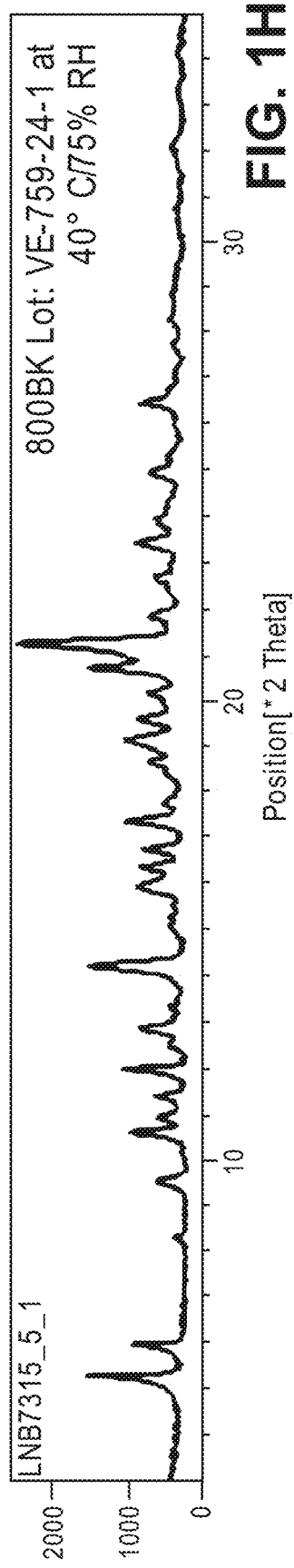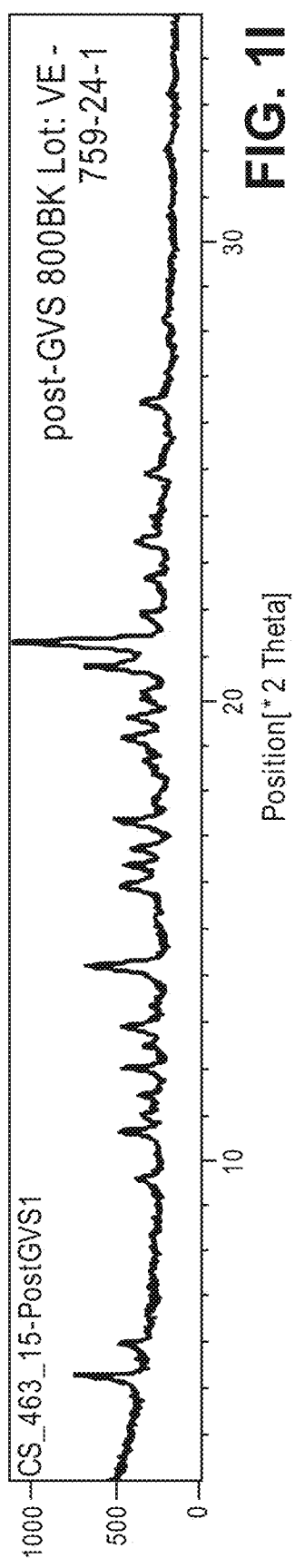

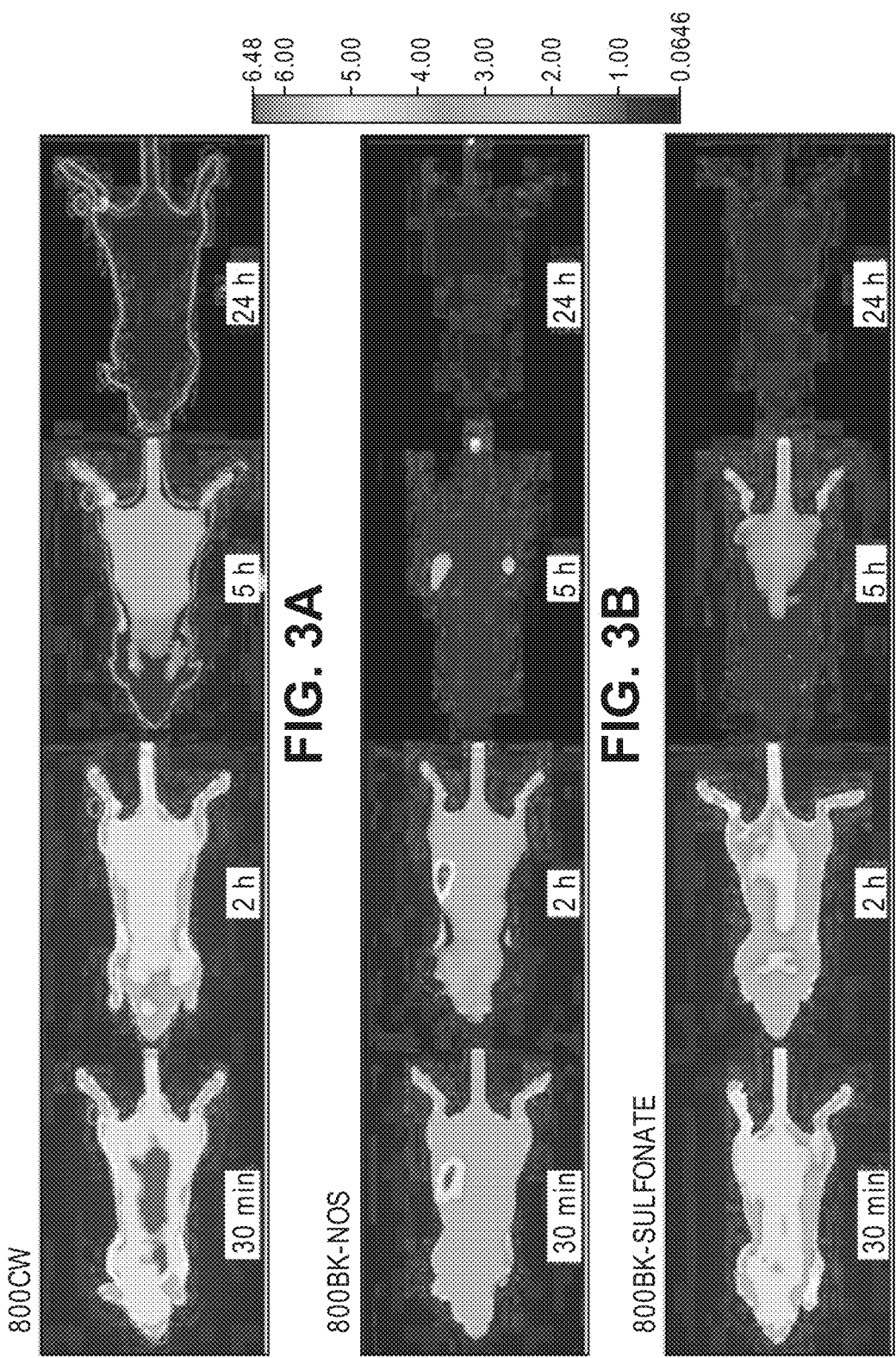

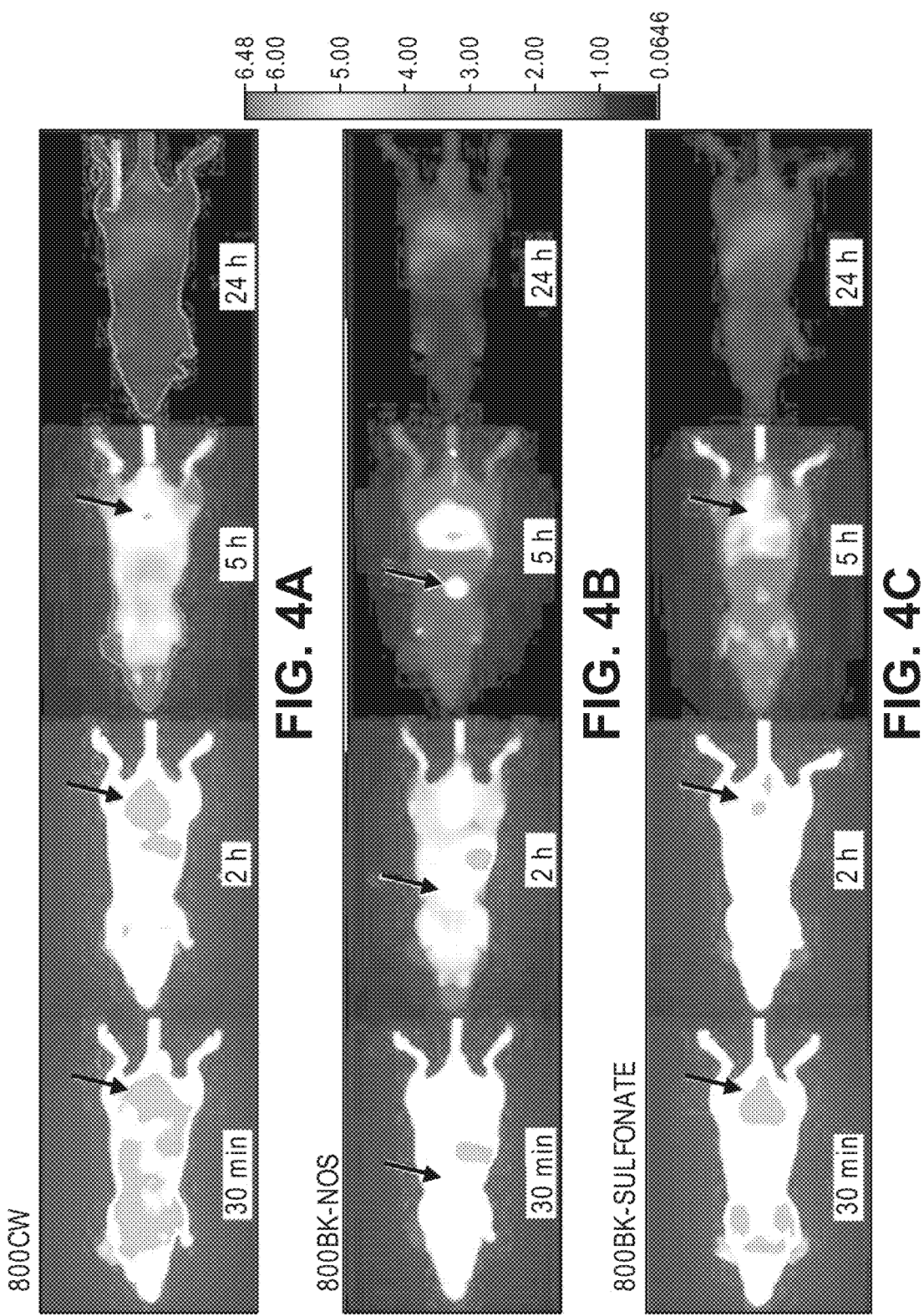

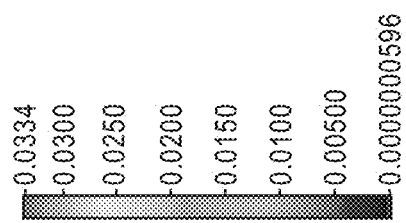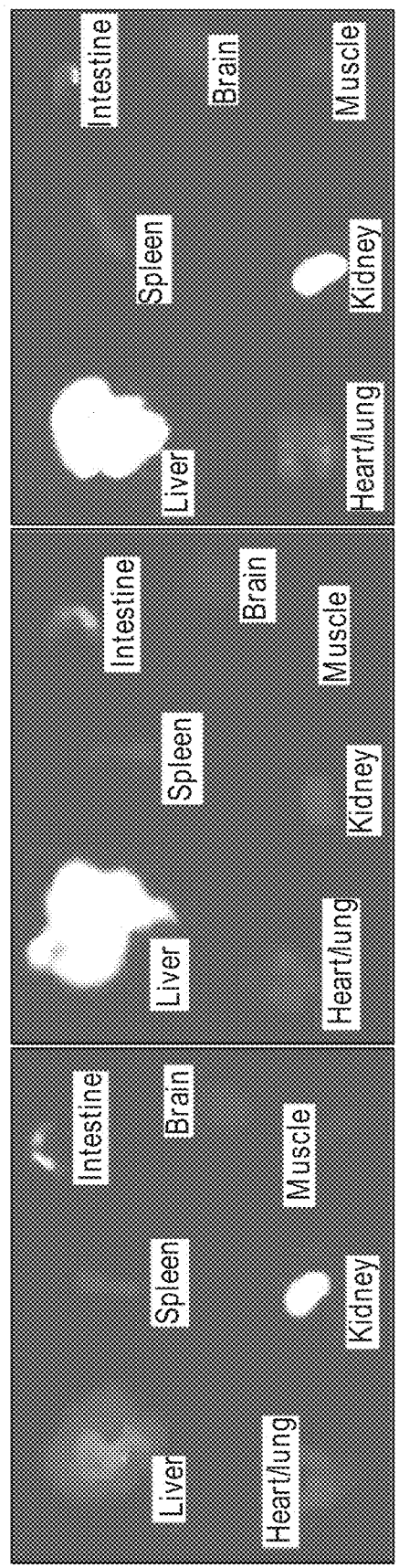
FIG. 6A  FIG. 6B  FIG. 6C

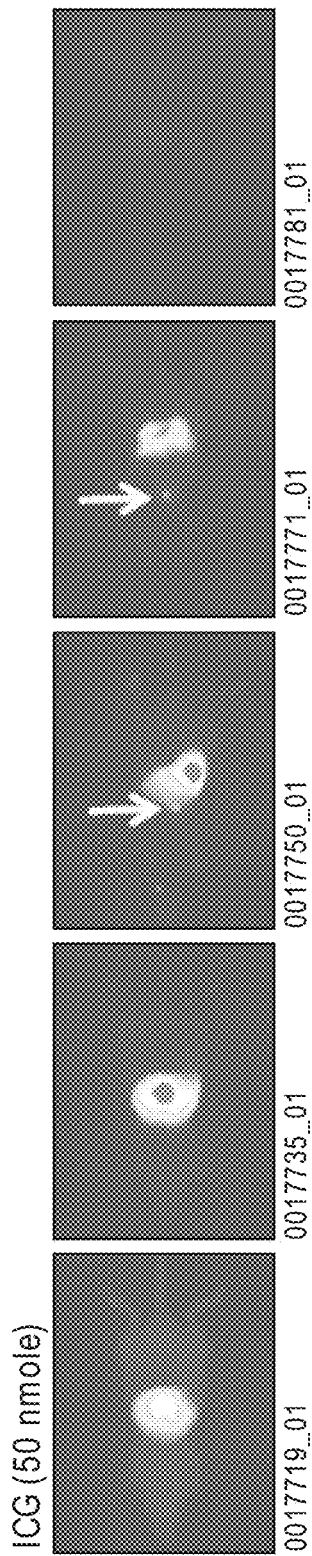
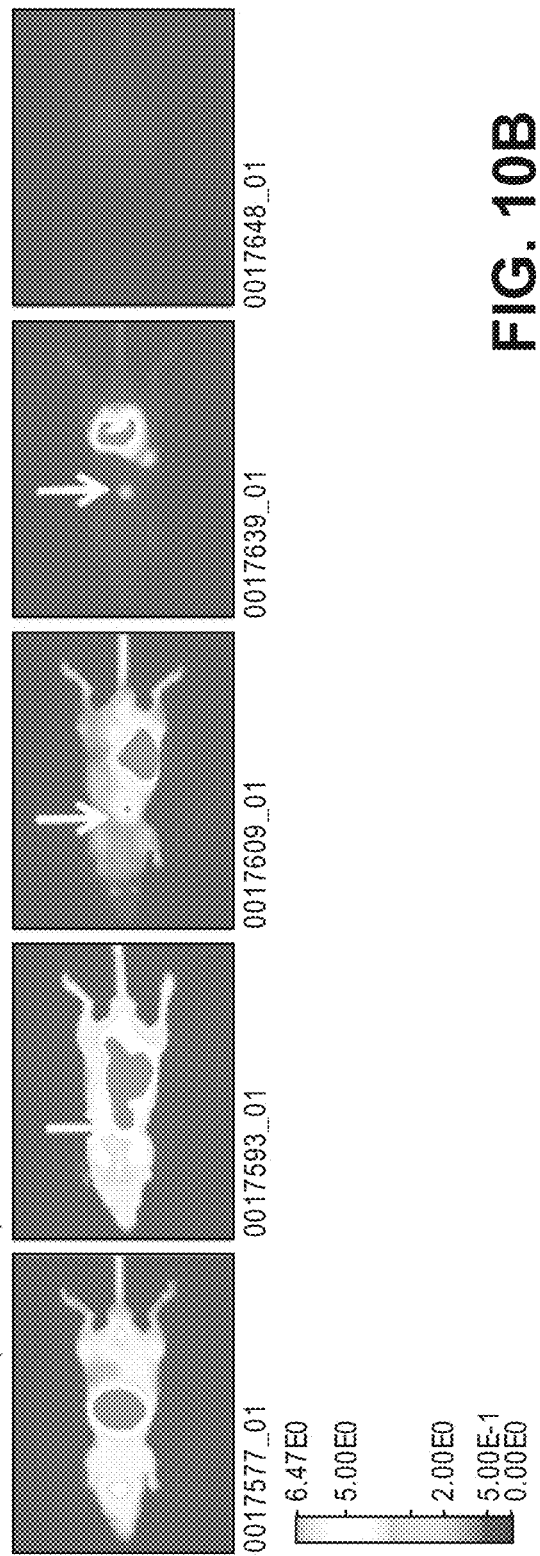
FIG. 10A
FIG. 10B

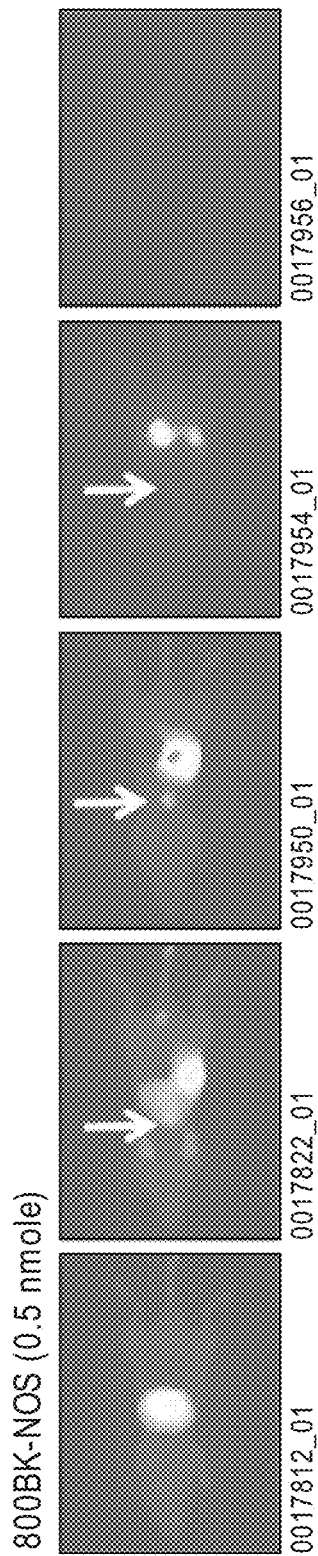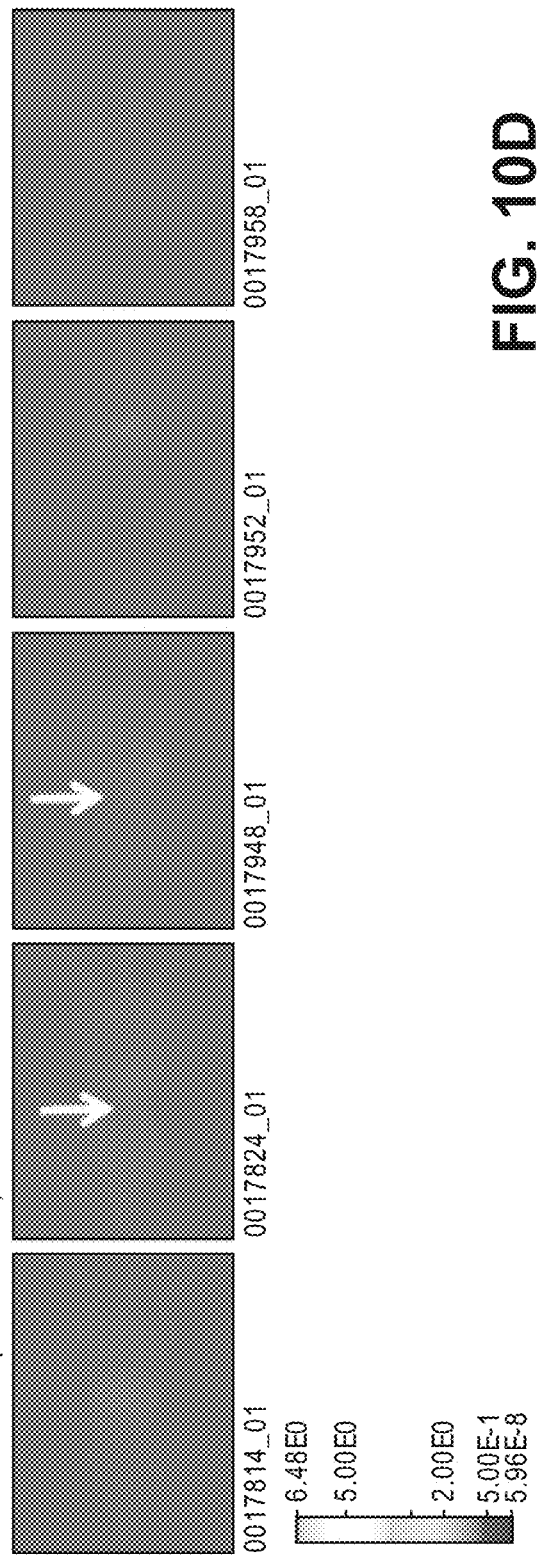
FIG. 10C
FIG. 10D

*Compound of Formula 2*

*Compound of Formula 1*

Dorsal   Ventral

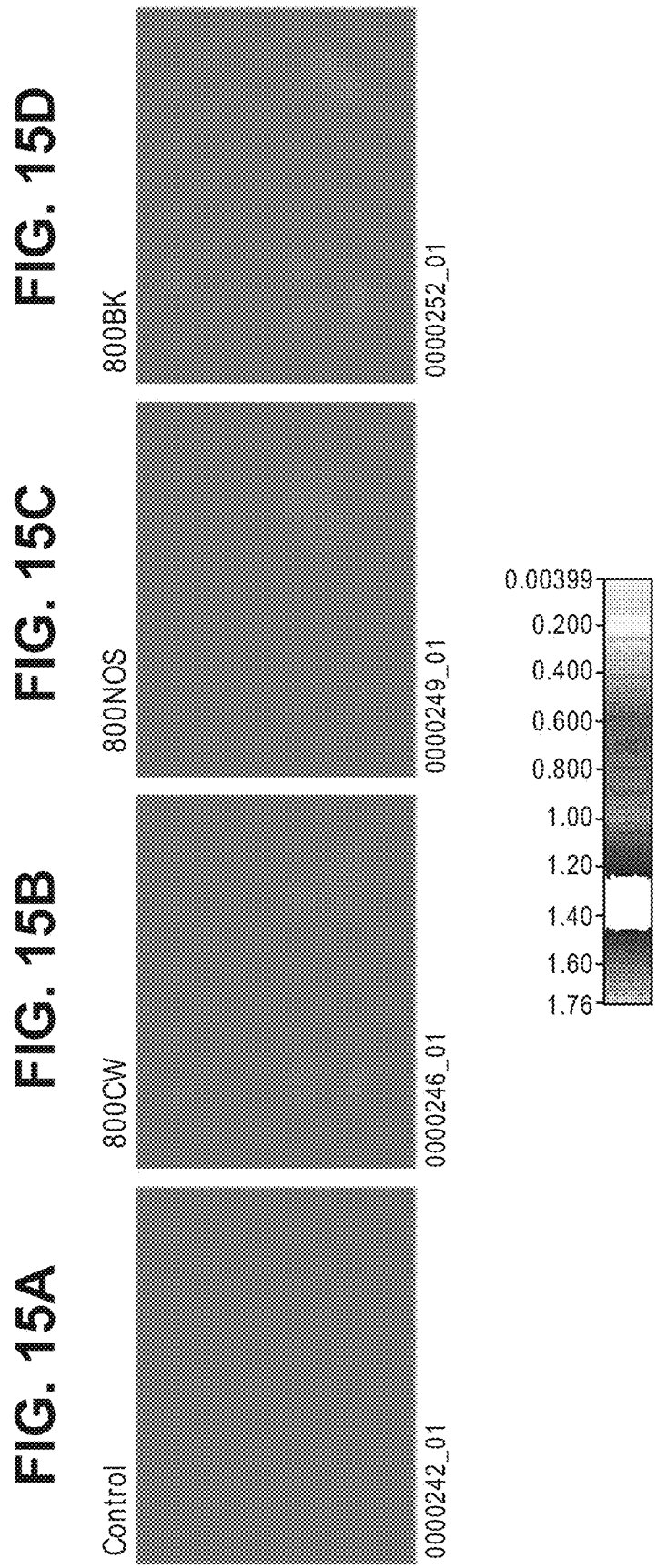

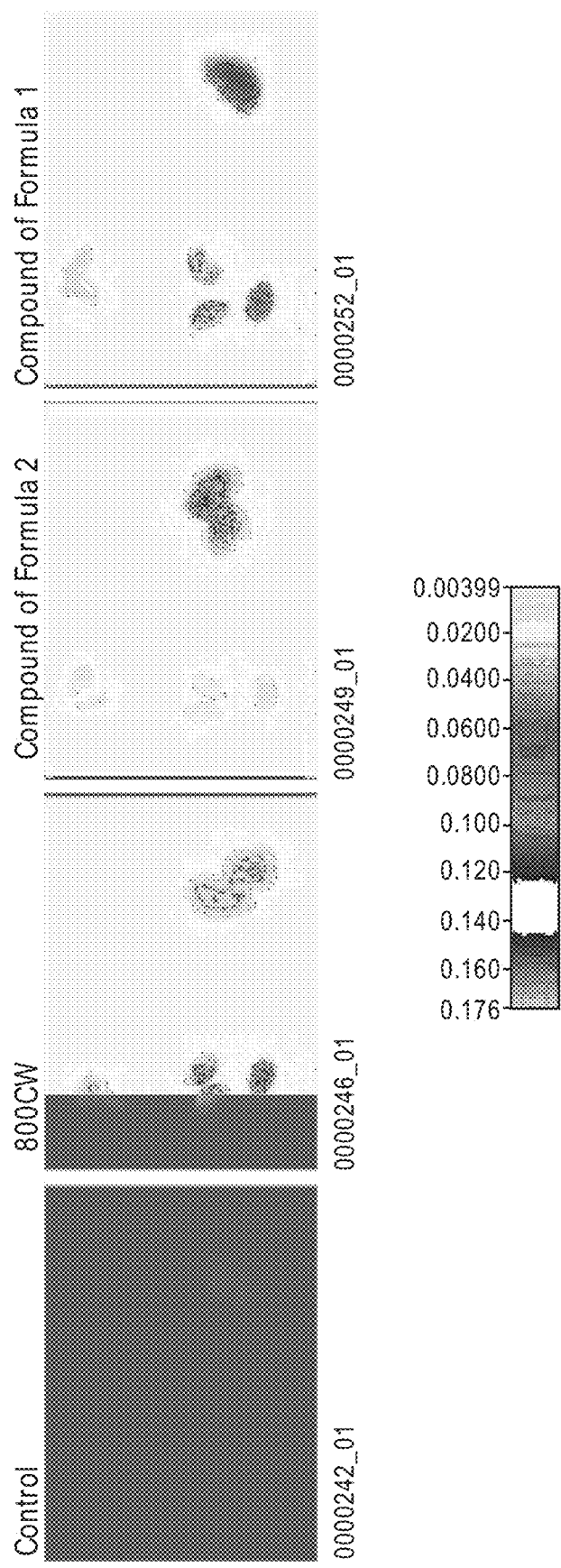

IR DYES FOR FLUORESCENCE IMAGING

CROSS-REFERENCE TO RELATED APPLICATIONS

This application is a continuation of U.S. patent application Ser. No. 14/949,654 filed Nov. 23, 2015, allowed, which application claims priority to U.S. Provisional Patent Application No. 62/084,971, filed Nov. 26, 2014, the teachings of which are hereby incorporated by reference in their entities for all purposes.

FIELD OF THE INVENTION

The present disclosure provides for methods of fluorescence imaging.

BACKGROUND OF THE INVENTION

Conventional laparoscopic and robotic laparoscopic techniques are both rapidly growing practices in the fields of colorectal and gynecologic surgery. Recent studies as described in Simorov et al., "Laparoscopic colon resection trends in utilization and rate of conversion to open procedure: a national database review of academic medical centers" *Ann Surg.* 2012 256(3), 462-468; Wright et al., "Robotically assisted vs laparoscopic hysterectomy among women with benign gynecologic disease" *JAMA* 2013 309 (7), 689-698; and, Park et al., "Ureteral injury in gynecologic surgery: a 5-year review in a community hospital" *Korean J. Urol.* 2012 53(2), 120-125, report 42% of all colorectal resections and greater than 30% of gynecologic procedures are attempted in this manner.

A laparoscopic approach offers several advantages over traditional open abdominal surgery, including decreased postoperative pain, shorter hospital length of stay, fewer surgical site infections, and decreased overall hospital cost, as described in Kiran et al., "Laparoscopic approach significantly reduces surgical site infections after colorectal surgery: data from national surgical quality improvement program" *J Am Coll Surg.* 2010 211(2) 232-238; Bilimoria et al., "Laparoscopic-assisted vs. open colectomy for cancer: comparison of short-term outcomes from 121 hospitals" *J Gastrointest Surg.* 2008 12(11) 2001-2009; Juo et al., "Is Minimally Invasive Colon Resection Better Than Traditional Approaches?: First Comprehensive National Examination With Propensity Score Matching" *JAMA Surg.* 2014 149(2) 177-184; Wilson et al., "Laparoscopic colectomy is associated with a lower incidence of postoperative complications compared with open colectomy: a propensity score-matched cohort analysis" *Colorectal Dis.* 5 2014 16(5) 382-389; Kobayashi et al., "Total laparoscopic hysterectomy in 1253 patients using an early ureteral identification technique" *J Obstet Gynaecol Res.* 2012 38(9) 1194-1200; Makinen et al., "Ten years of progress-improved hysterectomy outcomes in Finland 1996-2006: a longitudinal observation study" *BMJ Open* 2013 3(10) e003169.

However, limited tactile sensation and two-dimensional images can lead to iatrogenic ureter injury. Although infrequent, laparoscopic ureter injury remains a serious complication with significant associated morbidity. Reports indicate an incidence between 0.1-7.6% for colorectal and gynecologic surgery with more than 80% of these failing to be recognized intraoperatively, as described in Park et al.; Palaniappa et al., "Incidence of iatrogenic ureteral injury after laparoscopic colectomy" *Arch Surg.* 2012 147(3), 267-271; and, da Silva et al., "Role of prophylactic ureteric stents in colorectal surgery" *Asian J Endosc Surg.* 2012 5(3), 105-110. Current techniques for intraoperative ureter identification include ureteral stent placement, x-ray fluoroscopy, and visible dyes; however, both stents and fluoroscopy carry additional risk to the patient, and visible dyes are often not sensitive, as described in Tanaka et al., "Real-time intraoperative ureteral guidance using invisible near-infrared fluorescence" *J Urol.* 2007 178(5), 2197-2202; Bothwell et al., "Prophylactic ureteral catheterization in colon surgery. A five-year review" *Dis Colon Rectum.* 1994 37(4), 330-334; Wood et al., "Routine use of ureteric catheters at laparoscopic hysterectomy may cause unnecessary complications" *J Am Assoc Gynecol Laparosc.* 1996 3(3), 393-397; and, Brandes et al., "Diagnosis and management of ureteric injury: an evidence-based analysis" *BJU Int.* 2004 94(3), 277-289.

Fluorescence imaging using cyanine dyes is a rapidly emerging field to support surgical navigation and provide real-time illumination of anatomic structures. Emissions in the 700-900 nm range may avoid interference from tissue auto-fluorescence and can penetrate approximately 1 cm of tissue, as described in Adams et al., "Comparison of visible and near-infrared wavelength-excitable fluorescent dyes for molecular imaging of cancer" *J Biomed Opt.* 2007 12(2), 024017; and, Keereweer et al., "Optical Image-Guided Cancer Surgery: Challenges and Limitations" *Clin Cancer Res.* 2013 19(14), 3745-3754.

Another application of fluorescence imaging is for the real-time intra-operative imaging of the biliary anatomy, including the biliary duct and cystic duct. Current methods often use indocyanine green (ICG) dye by either intra-biliary injection or intravenous injection before surgery. However, studies have shown clear problems in using ICG dye. These include poor efficiency and kinetics of excretion into bile (Tanaka et al., "Real-time intraoperative assessment of the extrahepatic bile ducts in rats and pigs using invisible near-infrared fluorescent light" *Surgery* 2008 144(1) 39-48) and adverse reaction with the patient (Benya et al., "Adverse reactions to indocyanine green: a case report and a review of the literature" *Cathet Cardiovasc Diagn.* 1989 17(4) 231-233).

There exists a need for sensitive compositions and methods to detect and measure an internal target non-invasively. Specifically, there exists a need for improved, stable cyanine dyes to detect injuries to various organs that may occur during laparoscopic or robotic surgery. The present invention satisfies these and other needs.

BRIEF SUMMARY OF THE INVENTION

In an embodiment, the present invention includes a method for kidney ureter imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-(4-sulfonatophenoxy)cyclohex-1-en-1-yl)vinyl)-3,3-dimethyl-1-(4-sulfonatobutyl)-3H-indol-1-ium-5-sulfonate compound of Formula 1:

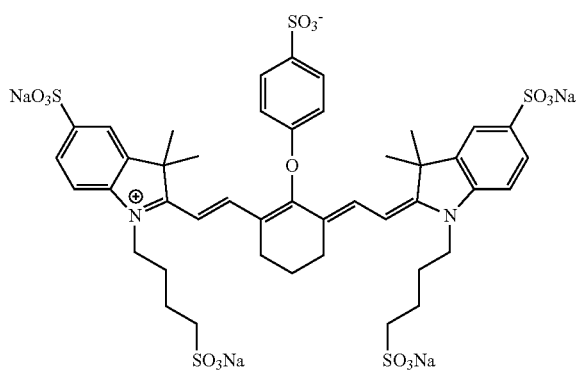

(1)

or a solvate or polymorph thereof and having a pharmaceutically acceptable cation, wherein the administering is performed at one or more times selected from the group consisting of before a procedure, during a procedure, after a procedure and combinations thereof, exposing tissue of the subject's renal system to electromagnetic radiation; and detecting fluorescence radiation from the compound.

In one embodiment, the method includes administering the compound of Formula 1 intravenously.

In one embodiment, the method includes administering the compound of Formula 1 wherein the pharmaceutically acceptable cation is selected from the group consisting of potassium or sodium.

In one embodiment, the method includes administering the compound of Formula 1 in combination with a pharmaceutically acceptable carrier selected from the group consisting of physiological sterile saline solution, sterile water solution, pyrogen-free water solution, isotonic saline solution, and phosphate buffer solution.

In one embodiment, the method includes administering the compound of Formula 1 at a diagnostic effective amount of the compound ranging between approximately 3000.0 μg/kg and approximately 1500.0 μg/kg.

In one embodiment, the method includes administering the compound of Formula 1 at a diagnostic effective amount of the compound ranging between approximately 1500.0 μg/kg and approximately 1000.0 μg/kg.

In one embodiment, the method includes administering the compound of Formula 1 at a diagnostic effective amount of the compound ranging between approximately 1000.0 μg/kg and approximately 500.0 μg/kg.

In one embodiment, the method includes administering the compound of Formula 1 at a diagnostic effective amount of the compound ranging between approximately 500.0 μg/kg and approximately 170.0 μg/kg.

In one embodiment, the method includes administering the compound of Formula 1 at a diagnostic effective amount of the compound ranging between approximately 170.0 μg/kg and approximately 120.0 μg/kg.

In one embodiment, the method includes administering the compound of Formula 1 at a diagnostic effective amount of the compound ranging between approximately 120.0 μg/kg and approximately 60.0 μg/kg.

In one embodiment, the method includes measuring a fluorescence intensity of the administered compound of Formula 1 remaining at the tissue of the subject's renal system at a time period after administering. In certain aspects, the methods provide visualizing the compound of Formula 1 in urine or bile.

In one embodiment, the method includes the measured fluorescence intensity of the administered compound of Formula 1 is background fluorescence approximately 24 hours after administering.

In one embodiment, the method includes the procedure selected from the group consisting of a laparoscopic procedure, a robotic procedure, a robotic laparoscopic procedure, and an open procedure.

In one embodiment, the method includes the measured fluorescence intensity of the administered compound of Formula 1 is higher in the kidney as compared to a measured fluorescence intensity of the administered compound of Formula 1 in one or more of the spleen, intestine, heart, lungs, muscle, or combinations thereof approximately up to six hours after administering.

In one embodiment, the present invention provides a solid form (a polymorph), which is Form A of Formula 1. Form A of Formula 1 has an X-ray powder diffraction pattern comprising a peak, in terms of 2-theta, at about 4.3°. Form A has an X-ray powder diffraction pattern comprising a peak, in terms of 2-theta, at about 4.3°, about 9.6°, about 12.9°, about 18.3°, and about 20.8°. Form A has an X-ray powder diffraction pattern substantially as shown in FIG. 1E.

In one embodiment, the present invention provides a method for biliary duct imaging, comprising administering a compound of Formula 1 to a subject; and detecting fluorescence radiation from the compound.

In another embodiment, the invention provides a polymorph or solid form (Form A) of the compound of Formula 1 in that it provides an XRPD pattern comprising peaks substantially as set out in Table 2.

In one embodiment, the present invention provides a solid form (a polymorph), which is Form B of Formula 1. Form B of Formula 1 has an X-ray powder diffraction pattern comprising a peak, in terms of 2-theta, at about 21.2°. Form B has an X-ray powder diffraction pattern comprising a peak, in terms of 2-theta, at about 5.3°, about 14.2°, about 14.3°, about 20.7°, and about 21.2°. Form B has an X-ray powder diffraction pattern substantially as shown in FIG. 1H.

In an embodiment, the invention includes a method for liver biliary imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate of Formula 2:

(2)

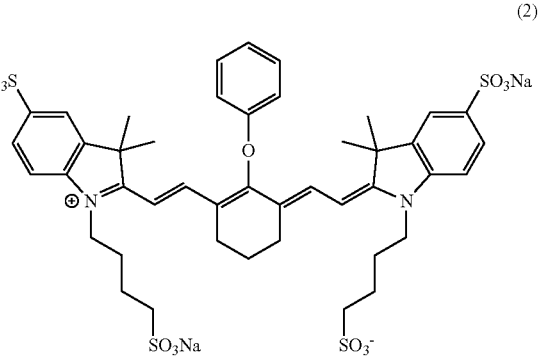

or a solvate or polymorph thereof and having a pharmaceutically acceptable cation, wherein the administering is performed at one or more times selected from the group consisting of before a procedure, during a procedure, after a procedure and combinations thereof, exposing tissue of the subject's liver system to electromagnetic radiation; and detecting fluorescence radiation emission from the compound.

In one embodiment, the method includes administering the compound of Formula 2 intravenously.

In one embodiment, the method includes administering the compound of Formula 2 wherein the pharmaceutically acceptable cation is selected from the group consisting of potassium or sodium.

In one embodiment, the method includes administering the compound of Formula 2 in combination with a pharmaceutically acceptable carrier selected from the group consisting of physiological sterile saline solution, sterile water solution, pyrogen-free water solution, isotonic saline solution, and phosphate buffer solution.

In one embodiment, the method includes administering the compound of Formula 2 at a diagnostic effective amount of the compound ranging between approximately 3000.0 µg/kg and approximately 1500.0 µg/kg.

In one embodiment, the method includes administering the compound of Formula 2 at a diagnostic effective amount of the compound ranging between approximately 1500.0 µg/kg and approximately 1000.0 µg/kg.

In one embodiment, the method includes administering the compound of Formula 2 at a diagnostic effective amount of the compound ranging between approximately 1000.0 µg/kg and approximately 500.0 µg/kg.

In one embodiment, the method includes administering the compound of Formula 2 at a diagnostic effective amount of the compound ranging between approximately 500.0 µg/kg and approximately 170.0 µg/kg.

In one embodiment, the method includes administering the compound of Formula 2 at a diagnostic effective amount of the compound ranging between approximately 170.0 µg/kg and approximately 120.0 µg/kg.

In one embodiment, the method includes administering the compound of Formula 2 at a diagnostic effective amount of the compound ranging between approximately 120.0 µg/kg and approximately 60.0 µg/kg.

In one embodiment, the method includes measuring a fluorescence intensity of the administered compound of Formula 2 remaining at the tissue of the subject's liver system at a time period after administering.

In certain aspects, the methods provide visualizing the compound of Formula 2 in urine or bile.

In one embodiment, the method includes the measured fluorescence intensity of the administered compound of Formula 2 is background fluorescence approximately 24 hours after administering.

In one embodiment, the method includes the procedure selected from the group consisting of a laparoscopic procedure, a robotic procedure, a robotic laparoscopic procedure, and an open procedure.

In one embodiment, the method includes the measured fluorescence intensity of the administered compound of Formula 2 is higher in the liver as compared to a measured fluorescence intensity of the administered compound of Formula 2 in one or more of the spleen, intestine, heart, lungs, muscle, or combinations thereof approximately up to six hours after administering.

In an embodiment, the invention includes a method for liver cystic duct imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate of Formula 2:

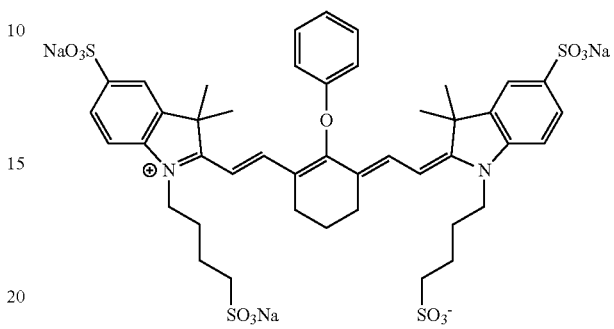

(2)

or a solvate or polymorph thereof and having a pharmaceutically acceptable cation, wherein the administering is performed at one or more times selected from the group consisting of before a procedure, during a procedure, after a procedure and combinations thereof, exposing tissue of the subject's liver system to electromagnetic radiation; and detecting fluorescence radiation from the compound.

In one embodiment, the method includes administering the compound of Formula 2 intravenously.

In one embodiment, the method includes administering the compound of Formula 2 wherein the pharmaceutically acceptable cation is selected from the group consisting of potassium or sodium.

In one embodiment, the method includes administering the compound of Formula 2 in combination with a pharmaceutically acceptable carrier selected from the group consisting of physiological sterile saline solution, sterile water solution, pyrogen-free water solution, isotonic saline solution, and phosphate buffer solution.

In one embodiment, the method includes administering the compound of Formula 2 at a diagnostic effective amount of the compound ranging between approximately 3000.0 µg/kg and approximately 1500.0 µg/kg.

In one embodiment, the method includes administering the compound of Formula 2 at a diagnostic effective amount of the compound ranging between approximately 1500.0 µg/kg and approximately 1000.0 µg/kg.

In one embodiment, the method includes administering the compound of Formula 2 at a diagnostic effective amount of the compound ranging between approximately 1000.0 µg/kg and approximately 500.0 µg/kg.

In one embodiment, the method includes administering the compound of Formula 2 at a diagnostic effective amount of the compound ranging between approximately 500.0 µg/kg and approximately 170.0 µg/kg.

In one embodiment, the method includes administering the compound of Formula 2 at a diagnostic effective amount of the compound ranging between approximately 170.0 µg/kg and approximately 120.0 µg/kg.

In one embodiment, the method includes administering the compound of Formula 2 at a diagnostic effective amount of the compound ranging between approximately 120.0 µg/kg and approximately 60.0 µg/kg.

In one embodiment, the method includes measuring a fluorescence intensity of the administered compound of Formula 2 remaining at the tissue of the subject's liver system at a time period after administering.

In one embodiment, the method includes the measured fluorescence intensity of the administered compound of Formula 2 is background fluorescence approximately 24 hours after administering.

In one embodiment, the method includes the procedure selected from the group consisting of a laparoscopic procedure, a robotic procedure, a robotic laparoscopic procedure, and an open procedure.

In one embodiment, the present invention provides a method for kidney ureter imaging, comprising administering a compound of Formula 2 to a subject; and detecting fluorescence radiation from the compound.

In one embodiment, the method includes the measured fluorescence intensity of the administered compound of Formula 2 is higher in the liver as compared to a measured fluorescence intensity of the administered compound of Formula 2 in one or more of the spleen, intestine, heart, lungs, muscle, or combinations thereof approximately up to six hours after administering.

In one embodiment, a pharmaceutical composition comprises a diagnostic imaging amount of a compound of Formula 1, a pharmaceutically acceptable cation, and a pharmaceutically acceptable carrier.

In one embodiment, the pharmaceutical composition comprising a diagnostic imaging amount of a compound of Formula 1, a pharmaceutically acceptable cation, and a pharmaceutically acceptable carrier is contained in an intravenous (IV) bag.

In one embodiment, a pharmaceutical composition comprises a diagnostic imaging amount of a compound of Formula 2, a pharmaceutically acceptable cation, and a pharmaceutically acceptable carrier.

In one embodiment, the pharmaceutical composition comprising a diagnostic imaging amount of a compound of Formula 2, a pharmaceutically acceptable cation, and a pharmaceutically acceptable carrier is contained in an intravenous (IV) bag.

In one embodiment, the invention includes a kit containing the pharmaceutical composition comprising a diagnostic imaging amount of a compound of Formula 1, a pharmaceutically acceptable cation, and a pharmaceutically acceptable carrier, and an instruction manual or instructions for use. The pharmaceutical composition can be contained in an intravenous (IV) bag.

In other embodiments, the invention includes a kit containing the pharmaceutical composition comprising a diagnostic imaging amount of a compound of Formula 2, a pharmaceutically acceptable cation, and a pharmaceutically acceptable carrier, and an instruction manual or instructions for use. The pharmaceutical composition can be contained in an intravenous (IV) bag.

In an embodiment, the invention includes a composition of matter comprising: 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate of Formula 2:

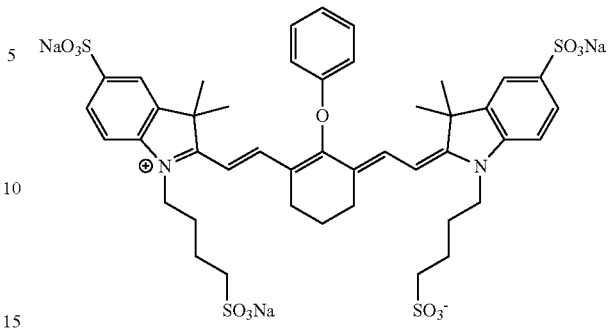

(2)

or a solvate or polymorph thereof and having a pharmaceutically acceptable cation.

Other embodiments, aspects, and objects will become better understood when read with the detailed description and drawings which follow.

BRIEF DESCRIPTION OF THE DRAWINGS

In each of the drawings 800CW corresponds to the compound set forth in Comparative example 1; 800BK-sulfonate refers to compound of Formula 1; 800BK-NOS refers to compound of Formula 2.

FIGS. 1A-1I show X-ray powder diffraction (XRPD) patterns forvarious samples. Samples shown in FIGS. 1A and 1C represent Form A. FIG. 1B is Form A, but less crystalline. FIGS. 1D and 1E show the XRPD pattern of crystalline Form A. FIG. 1F shows the XRPD of the amorphous form. FIG. 1H and FIG. 1I show the XRPD pattern of crystalline Form B. For comparison, FIG. 1G is identical to FIG. 1D.

FIGS. 3A-C illustrates dorsal view fluorescence images of mice for the compound of comparative example 1 (FIG. 3A), the compound of Formula 1 (FIG. 3B), and the compound of Formula 2 (FIG. 3C) probes. Images are presented for the approximate time points post probe administration: 30 min, 2 hrs, 5 hrs, and 24 hrs. A Pearl® Impulse small animal imaging system was used for all animal and organ image acquisitions FIGS. 4A-C illustrate ventral view fluorescence images of the same mice for the compound of comparative example 1 (FIG. 4A); the compound of Formula 1 (FIG. 4B), and the compound of Formula 2 probes (FIG. 4C). Images are presented for the approximate time points post probe administration: 30 min, 2 hrs, 5 hrs, and 24 hrs. Arrows pinpoint bladder regional bladder signal. White arrows point to gall bladder signal.

FIGS. 6A-D show fluorescence data for mouse organs for the compound of comparative example 1 (FIG. 6A), the compound of Formula 2 (FIG. 6B), the compound of Formula 1 (FIG. 6C): liver, spleen, intestine, brain, heart/lung, kidney, brain, and muscle (FIG. 6D). Fluorescence signal (800 nm) adjusted to area (pixel) for all probes.

FIGS. 10A, 10B, 10C, 10D, and 10E illustrate biliary tract imaging for: 50 nmole of ICG in phosphate buffer saline (PBS) solution (FIG. 10A), 1 nmole of the compound of Formula 2 in PBS solution (FIG. 10B), 0.5 nmole of the compound of Formula 2 in PBS solution (FIG. 10C), and 0.1 nmole of the compound of Formula 2 in PBS solution (FIGS. 10D and 10E). The imaging areas displayed for each condition were recorded at 1 min, 30 min, 2 hrs, 5 hrs, and 24 hrs., respectively (left to right).

FIGS. 11F-11H show intraoperative fluorescence (800 nm, compound of Formula 2) (FIG. 11G), white light (FIG. 11F), and composite images of the liver, gall bladder, and bile duct for compound of Formula 2 (0.1 nmole) (FIG. 11H).

FIGS. 15A-15D show the signal intensity of the kidney (lower left corner), liver (lower right corner), lungs (upper left corner) and muscle (upper right corner) on the organ $1/10^{th}$ LUT scale. Organs from an animal injected with no probe (control), 800CW dye, 800NOS dye, and 800BK dye are shown in FIG. 15A, FIG. 15B, FIG. 15C, and FIG. 15D, respectively.

FIGS. 16A-16D show the signal intensity of the kidney (lower left corner), liver (lower right corner), lungs (upper left corner) and muscle (upper right corner) on the organ $1/100^{th}$ LUT scale. Organs from an animal injected with no probe (control), 800CW dye, 800NOS dye, and 800BK dye are shown in FIG. 16A, FIG. 16B, FIG. 16C, and FIG. 16D, respectively.

DETAILED DESCRIPTION OF THE INVENTION

I. Definitions

Figure 1A:
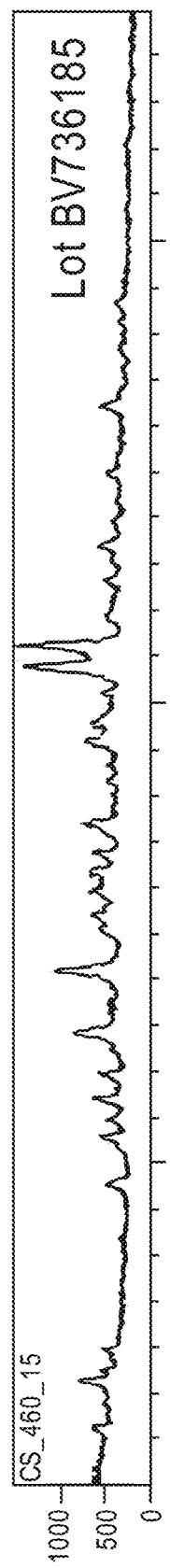

The terms "a," "an," or "the" as used herein not only include aspects with one member, but also include aspects with more than one member. For example, an embodiment of a method of imaging that comprises using a compound set forth herein would include an aspect in which the method comprises using two or more compounds set forth herein.

The term "approximately" or "about" as used herein to modify a numerical value indicates a defined range around that value. If "X" were the value, "approximately X" or "about X" would indicate a value from 0.9X to 1.1X, and more preferably, a value from 0.95X to 1.05X. Any reference to "approximately X" or "about X" specifically indicates at least the values X, 0.95X, 0.96X, 0.97X, 0.98X, 0.99X, 1.01X, 1.02X, 1.03X, 1.04X, and 1.05X. For example, "approximately X" or "about X" is intended to teach and provide written description support for a claim limitation of, e.g., "0.98X."

When the quantity "X" only allows whole-integer values (e.g., "X carbons") and X is at most 15, "about X" indicates from (X−1) to (X+1). In this case, "about X" as used herein specifically indicates at least the values X, X−1, and X+1. If X is at least 16, the values of 0.90X and 1.10X are rounded to the nearest whole-integer values to define the boundaries of the range.

When the modifier "approximately" or "about" is applied to describe the beginning of a numerical range, it applies to both ends of the range. Thus, "from approximately 700 to 850 nm" is equivalent to "from approximately 700 nm to approximately 850 nm." Thus, "from about 700 to 850 nm" is equivalent to "from about 700 nm to about 850 nm." When "approximately" or "about" is applied to describe the first value of a set of values, it applies to all values in that set. Thus, "about 680, 700, or 750 nm" is equivalent to "about 680 nm, about 700 nm, or about 750 nm."

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring, a cationic counterion (e.g., the cation of a Group I metal such as sodium) must be added to balance the negative charge from additional sulfonato groups. Similarly, anionic counterions must be added to balance any additional cationic groups (e.g., most basic amino groups under physiological conditions).

II. Embodiments

While preferred embodiments of the invention are shown and described herein, such embodiments are provided by way of example only and are not intended to otherwise limit the scope of the invention. Various alternatives to the described embodiments of the invention may be employed in practicing the invention.

Some advantages of cyanine dyes include: (1) cyanine dyes strongly absorb and fluoresce light; (2) many cyanine dyes do not rapidly photo-bleach under the fluorescence microscope; (3) many structures and synthetic procedures are available and the class of dyes is versatile; and (4)

cyanine dyes are relatively small (a typical molecular weight is about 1,000 daltons) so they do not cause appreciable steric interference.

Generally, cyanine dyes are prepared according to the procedures taught in Hamer, F. M., *Cyanine Dyes and Related Compounds*, Weissberger, Mass., ed. Wiley Interscience, N.Y. 1964. For example, U.S. Pat. Nos. 6,663,847; 6,887,854; 6,995,274; 7,504,089; 7,547,721; 7,597,878 and 8,303,936, incorporated herein by reference, describe synthesis mechanisms for a variety of cyanine dyes.

Other cyanine dyes are known which contain reactive functional groups. For example, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

As described herein, the present invention provides for the use of a cyanine dye of the compound having Formula 1:

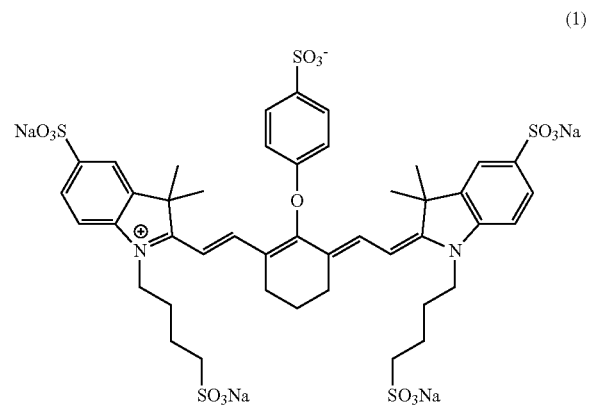

(1)

or a solvate or polymorph thereof and having a pharmaceutically acceptable cation.

In one embodiment, the present invention provides a solid form (a polymorph), which is Form A of Formula 1. Form A of Formula 1 has an X-ray powder diffraction pattern comprising a peak, in terms of 2-theta, at about 4.30. Form A has an X-ray powder diffraction pattern comprising a peak, in terms of 2-theta, at about 4.3°, about 9.6°, about 12.9°, about 18.3°, and about 20.8°. Form A has an X-ray powder diffraction pattern substantially as shown in FIG. 1E.

In one embodiment, the present invention provides a solid form (a polymorph), which is Form B of Formula 1. Form B of Formula 1 has an X-ray powder diffraction pattern comprising a peak, in terms of 2-theta, at about 21.2°. Form B has an X-ray powder diffraction pattern comprising a peak, in terms of 2-theta, at about 5.3°, about 14.2°, about 14.3°, about 20.7° and about 21.2°. Form B has an X-ray powder diffraction pattern substantially as shown in FIG. 1H.

In certain aspects, the polymorphs of the invention are formulated into a composition prior to administration to a subject.

The compounds of Formula 1 can exist in crystalline or noncrystalline form, or as a mixture thereof. For salts of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethylacetate. In one embodiment, the invention provides the sodium salt of the compound of Formula 1 incorporated into the crystalline lattice.

In one aspect, the present invention provides a polymorph of the compound of Formula 1 in isolated or pure form. "Isolated" or "pure" or "substantially pure" form refers to a sample in which the polymorph is present in an amount of >75%, particularly >90%, >91%, >92%, >93%, >94%, >95%, >96%, >97%, >98%, or >99%, relative to other materials which may be present in the sample.

The polymorphs made according to the methods of the invention can be characterized by any methodology according to the art. For example, the polymorphs made according to the methods of the invention may be characterized by X-ray powder diffraction (XRPD), differential scanning calorimetry (DSC), thermogravimetric analysis (TGA), hot-stage microscopy, and spectroscopy (e.g., Raman, solid state nuclear magnetic resonance (ssNMR), and infrared (IR)).

XRPD

Polymorphs according to the invention may be characterized by X-ray powder diffraction patterns (XRPD). The relative intensities of XRPD peaks can vary, depending upon the sample preparation technique, the sample mounting procedure and the particular instrument employed. Moreover, instrument variation and other factors can affect the 2θ values. Therefore, the XRPD peak assignments can vary by plus or minus about 0.2 degrees.

The polymorph forms of the invention are useful in the production of imaging agents and can be obtained by means of a crystallization process to produce crystalline and semi-crystalline forms. In various embodiments, the crystallization is carried out by either generating the compound of Formula 1 in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. The crystallization can be followed by drying carried out under controlled conditions until the desired water content is reached in the end polymorphic form.

In another embodiment, the present invention provides a method of making a polymorph of a compound of Formula 1 (Form A or Form B). In various embodiments, the invention is directed to methods of making a polymorph of the compound of Formula 1, wherein the method involves converting an amorphous form into a desired polymorph. In certain embodiments, the methods comprise exposing a composition comprising an amorphous form to conditions sufficient to convert at least about 50% of the total amount of the amorphous form into at least about 50% of the desired polymorph, and isolating the desired polymorph as needed.

In certain instances, a crystalline solid will be more amenable to purification than an amorphous solid and the crystalline form is able to be made in higher purity. This is because, under proper conditions, the formation of the crystals tends to exclude impurities from the solid, in contrast to amorphous solids formed in a less controlled manner. Similarly, a crystalline solid will often have better stability than an amorphous solid, as the crystal packing gives a protective effect. For materials which are polymorphic, some crystal forms will normally be more effective than others at excluding impurities and enhancing stability.

In one embodiment, the present invention provides for a composition according to Formula 2:

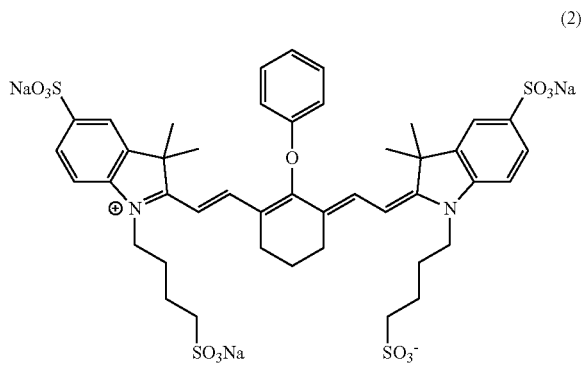

(2)

or a hydrate or polymorph thereof and having a pharmaceutically acceptable cation.

One embodiment of the invention includes a method for organ imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-(4-sulfonatophenoxy)cyclohex-1-en-1-yl)vinyl)-3,3-dimethyl-1-(4-sulfonatobutyl)-3H-indol-1-ium-5-sulfonate compound of Formula 1:

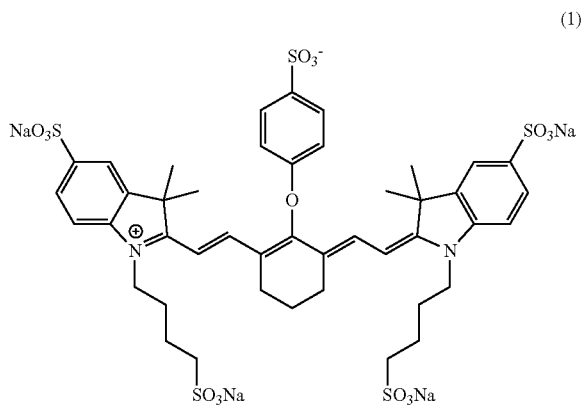

(1)

or a solvate or polymorph thereof and having a pharmaceutically acceptable cation, wherein the administering is performed at one or more times selected from the group consisting of before a procedure, during a procedure, after a procedure and combinations thereof, exposing tissue of the subject's organ system to electromagnetic radiation; and detecting fluorescence radiation from the compound. In one embodiment, the organ includes one or more of kidney, bladder, liver, spleen, intestine, heart, lungs and muscle. In one embodiment, the organ is kidney, bladder or combinations of. In another embodiment, the organ is the ureter of a kidney.

In one embodiment, the method includes administering the compound of Formula 1 intravenously. The compound of Formula 1 can be administered as a bolus injection, e.g., an intravenous bolus injection. In some embodiments, about 5 mL to about 10 mL of a composition comprising the compound of Formula 1 is administered in a bolus injection.

In one embodiment, the method includes administering the compound of Formula 1 wherein the pharmaceutically acceptable cation is selected from the group consisting of potassium or sodium.

In one embodiment, the method includes administering the compound of Formula 1 in combination with a pharmaceutically acceptable carrier selected from the group consisting of physiological sterile saline solution, sterile water solution, pyrogen-free water solution, isotonic saline solution, and phosphate buffer solution.

The compound of Formula 1 can be highly soluble in water. In some embodiments, the compound of Formula 1 is re-suspended in water to a concentration of at least 200 mg/mL, or about 300 mg/mL to about 320 mg/mL.

In one embodiment, the method includes administering the compound of Formula 1 at a diagnostic effective amount of the compound ranging between approximately 3000.0 µg/kg and approximately 1500.0 µg/kg.

In one embodiment, the method includes administering the compound of Formula 1 at a diagnostic effective amount of the compound ranging between approximately 1500.0 µg/kg and approximately 1000.0 µg/kg.

In one embodiment, the method includes administering the compound of Formula 1 at a diagnostic effective amount of the compound ranging between approximately 1000.0 µg/kg and approximately 500.0 µg/kg.

In one embodiment, the method includes administering the compound of Formula 1 at a diagnostic effective amount of the compound ranging between approximately 500.0 µg/kg and approximately 170.0 µg/kg.

In one embodiment, the method includes administering the compound of Formula 1 at a diagnostic effective amount of the compound ranging between approximately 170.0 rig/kg and approximately 120.0 µg/kg.

In one embodiment, the method includes administering the compound of Formula 1 at a diagnostic effective amount of the compound ranging between approximately 120.0 µg/kg and approximately 60.0 µg/kg.

In one embodiment, the method includes administering the compound of Formula 1 at a diagnostic effective amount of the compound ranging between approximately 30.0 µg/kg and approximately 500.0 µg/kg.

The compounds of Formula 1 can be non-toxic. They can absorb and fluoresce light, and do not rapidly photo-bleach under fluorescence imaging. Upon administration, the compounds of Formula 1 can be transported to tissues and organs of the subject via the natural flow of bodily fluids in the subject. As such, compounds of Formula 1 can be carried or transferred from the site of administration to the desired sites, tissues and organs for, e.g., visualization.

In certain embodiments, the compounds and methods herein can image the biliary tract which includes any part of the liver, gall bladder, spleen, small intestine, and associated ducts. In certain instances, the biliary tract includes the intrahepatic bile ducts, cystic duct-gallbladder to common bile duct—and common bile duct—liver and gallbladder to small intestine. In some instances, the compounds herein are found in a subject's bile or urine at a time period after administering. The present invention provides compositions of the compounds of Formula 1 or 2 in urine or bile.

In certain embodiments, the methods herein provide visualizing the compounds of Formula 1 or 2 in urine or bile.

In one embodiment, the method includes measuring a fluorescence intensity of the administered compound of Formula 1 remaining at the tissue of the subject's organ at a time period after administering. In one embodiment, the organ includes one or more of kidney, bladder, liver, gall bladder, spleen, intestine, heart, lungs and muscle. In one embodiment, the organ is kidney, bladder or combinations. In another embodiment, the organ is the ureter of a kidney. In some embodiments, the method includes measuring a fluorescence intensity of the administered compound of Formula 1 remaining in the subject's urine or bile at a time period after administering.

In one embodiment, the method includes the measured fluorescence intensity of the administered compound of Formula 1 is background fluorescence approximately 24 hours after administering.

In one embodiment, the method includes the procedure selected from the group consisting of a laparoscopic procedure, a robotic procedure, a robotic laparoscopic procedure, an endoscopic procedure, and an open procedure.

In one embodiment, the method includes the measured fluorescence intensity of the administered compound of Formula 1 is higher in the kidney as compared to a measured fluorescence intensity of the administered compound of Formula 1 in one or more of the spleen, intestine, heart, lungs, muscle, or combinations thereof approximately up to six hours after administering.

In one embodiment, a pharmaceutical composition comprises a diagnostic imaging amount of a compound of Formula 1, a pharmaceutically acceptable cation, and a pharmaceutically acceptable carrier.

In another embodiment, a method for organ imaging, comprising: administering to a subject a diagnostic effective amount of 2-((E)-2-((E)-3-(2-((E)-3,3-dimethyl-5-sulfonato-1-(4-sulfonatobutyl)indolin-2-ylidene)ethylidene)-2-phenoxycyclohex-1-en-1-yl)vinyl)-3,3-dimethyl-1-(4-sulfonatobutyl)-3H-indol-1-ium-5-sulfonate of Formula 2:

(2)

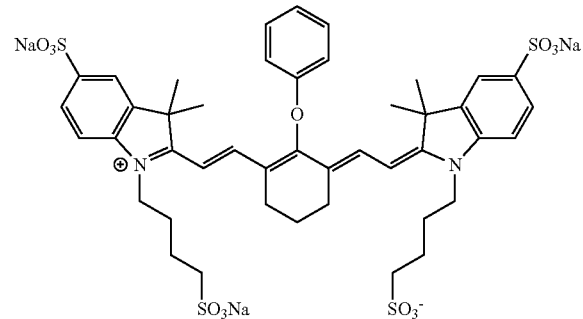

or a solvate or polymorph thereof and having a pharmaceutically acceptable cation, wherein the administering is performed at one or more times selected from the group consisting of before a procedure, during a procedure, after a procedure and combinations thereof, exposing tissue of the subject's organ system to electromagnetic radiation; and detecting fluorescence radiation from the compound. In one embodiment, the organ includes one or more of kidney, bladder, liver, spleen, intestine, heart, lungs and muscle. In one embodiment, the organ is a liver. In one embodiment, the organ is the biliary duct of a liver. In one embodiment, the organ is the cystic duct of a liver.

In one embodiment, the method includes administering the compound of Formula 2 intravenously. The compound of Formula 2 can be administered as a bolus injection, e.g., an intravenous bolus injection. In some embodiments, about 5 mL to about 10 mL of a composition comprising the compound of Formula 2 is administered in a bolus injection.

In one embodiment, the method includes administering the compound of Formula 2 wherein the pharmaceutically acceptable cation is selected from the group consisting of potassium or sodium.

In one embodiment, the method includes administering the compound of Formula 2 in combination with a pharmaceutically acceptable carrier selected from the group consisting of physiological sterile saline solution, sterile water solution, pyrogen-free water solution, isotonic saline solution, and phosphate buffer solution.

The compound of Formula 2 can be highly soluble in water. In some embodiments, the compound of Formula 2 is resuspended in water to a concentration of at least 200 mg/mL, about 300 mg/mL or about 320 mg/mL.

In one embodiment, the method includes administering the compound of Formula 2 at a diagnostic effective amount of the compound ranging between approximately 3000.0 μg/kg and approximately 1500.0 μg/kg.

In one embodiment, the method includes administering the compound of Formula 2 at a diagnostic effective amount of the compound ranging between approximately 1500.0 μg/kg and approximately 1000.0 μg/kg.

In one embodiment, the method includes administering the compound of Formula 2 at a diagnostic effective amount of the compound ranging between approximately 1000.0 μg/kg and approximately 500.0 μg/kg.

In one embodiment, the method includes administering the compound of Formula 2 at a diagnostic effective amount of the compound ranging between approximately 500.0 μg/kg and approximately 170.0 μg/kg.

In one embodiment, the method includes administering the compound of Formula 2 at a diagnostic effective amount of the compound ranging between approximately 170.0 μg/kg and approximately 120.0 μg/kg.

In one embodiment, the method includes administering the compound of Formula 2 at a diagnostic effective amount of the compound ranging between approximately 120.0 μg/kg and approximately 60.0 μg/kg.

In one embodiment, the method includes administering the compound of Formula 2 at a diagnostic effective amount of the compound ranging between approximately 30.0 μg/kg and approximately 500.0 μg/kg.

The compounds of Formula 2 can be non-toxic. They can absorb and fluoresce light, and do not rapidly photo-bleach under fluorescence imaging. Upon administration, the compounds of Formula 2 can be transported to tissues and organs of the subject via the natural flow of bodily fluids in the subject. As such, compounds of Formula 2 can be carried or transferred from the site of administration to the desired sites, tissues and organs for, e.g., visualization.

In one embodiment, the method includes measuring a fluorescence intensity of the administered compound of Formula 2 remaining at the tissue of the subject's organ system at a time period after administering. In one embodiment, the organ includes one or more of kidney, bladder, liver, gall bladder, spleen, intestine, heart, lungs and muscle. In one embodiment, the organ is the liver. In another embodiment, the organ is the biliary duct of a liver. In another embodiment, the organ is the cystic duct of a liver. In some embodiments, the method includes measuring a fluorescence intensity of the administered compound of Formula 2 remaining in the subject's urine or bile at a time period after administering.

In one embodiment, the method includes the measured fluorescence intensity of the administered compound of Formula 2 is background fluorescence approximately 24 hours after administering.

In one embodiment, the method includes the procedure selected from the group consisting of a laparoscopic procedure, a robotic procedure, a robotic laparoscopic procedure, an endoscopic procedure, and an open procedure.

In one embodiment, the method includes the measured fluorescence intensity of the administered compound of Formula 2 is higher in the liver as compared to a measured fluorescence intensity of the administered compound of Formula 2 in one or more of the spleen, intestine, heart, lungs, muscle, or combinations thereof approximately up to six hours after administering.

In one embodiment, a pharmaceutical composition comprises a diagnostic imaging amount of a compound of Formula 2, a pharmaceutically acceptable cation, and a pharmaceutically acceptable carrier.

In some embodiments, a pharmaceutical composition of compound of Formula 1 or compound of Formula 2 are in combination with a pharmaceutically acceptable cation and a pharmaceutically acceptable carrier in a diagnostic effective amount. In such embodiments, the pharmaceutical composition is contained in an intravenous drip bag.

In selected embodiments, the diagnostic effective amount of each of the compound of Formula 1 and the compound of Formula 2, is independently less than, for example, 3000.0, 2800.0, 2600.0, 2400.0, 2200.0, 2000.0, 1800.0, 1600.0, 1400.0, 1200.0, 1000.0, 950.0, 900.0, 850.0, 800.0, 750.0, 700.0, 650.0, 600.0, 550.0, 500.0, 490.0, 480.0, 470.0, 460.0, 450.0, 440.0, 430.0, 420.0, 410.0, 400.0, 390.0, 380.0, 370.0, 360.0, 350.0, 340.0, 330.0, 320.0, 310.0, 300.0, 290.0, 280.0, 270.0, 260.0, 250.0, 240.0, 230.0, 220.0, 210.0, 200.0, 190.0, 180.0, 170.0, 160.0, 150.0, 140.0, 130.0, 120.0, 110.0, 100.0, 95.0, 90.0, 85.0, 80.0, 75.0, 70.0, 65.0, 60.0, 55.0, 50.0, 49.0, 48.0, 47.0, 46.0, 45.0, 44.0, 43.0, 42.0, 41.0, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.9, 30.8, 30.7, 30.6, 30.5, 30.4, 30.3, 30.2, 30.1 µg/kg.

In selected embodiments, the diagnostic effective amount of each of the compound of Formula 1 and the compound of Formula 2, is independently greater than, for example, 2800.0, 2600.0, 2400.0, 2200.0, 2000.0, 1800.0, 1600.0, 1400.0, 1200.0, 1000.0, 950.0, 900.0, 850.0, 800.0, 750.0, 700.0, 650.0, 600.0, 550.0, 500.0, 490.0, 480.0, 470.0, 460.0, 450.0, 440.0, 430.0, 420.0, 410.0, 400.0, 390.0, 380.0, 370.0, 360.0, 350.0, 340.0, 330.0, 320.0, 310.0, 300.0, 290.0, 280.0, 270.0, 260.0, 250.0, 240.0, 230.0, 220.0, 210.0, 200.0, 190.0, 180.0, 170.0, 160.0, 150.0, 140.0, 130.0, 120.0, 110.0, 100.0, 95.0, 90.0, 85.0, 80.0, 75.0, 70.0, 65.0, 60.0, 55.0, 50.0, 49.0, 48.0, 47.0, 46.0, 45.0, 44.0, 43.0, 42.0, 41.0, 40.0, 39.5, 39.0, 38.5, 38.0, 37.5, 37.0, 36.5, 36.0, 35.5, 35.0, 34.5, 34.0, 33.5, 33.0, 32.5, 32.0, 31.5, 31.0, 30.9, 30.8, 30.7, 30.6, 30.5, 30.4, 30.3, 30.2, 30.1, 30.0 µg/kg.

In selected embodiments, the diagnostic effective amount of each of the compound of Formula 1 and the compound of Formula 2, is independently in the range from approximately 30.0 µg/kg to approximately 3000.0 µg/kg, approximately 30.1 µg/kg to approximately 2800.0 jg/kg, approximately 30.2 µg/kg to approximately 2600.0 µg/kg, approximately 30.3 µg/kg to approximately 2400.0 µg/kg, approximately 30.4 µg/kg to approximately 2200.0 µg/kg, approximately 30.5 µg/kg to approximately 2000.0 µg/kg, approximately 30.6 µg/kg to approximately 1800.0 µg/kg, approximately 30.7 µg/kg to approximately 1600.0 µg/kg, approximately 30.8 µg/kg to approximately 1400.0 µg/kg, approximately 30.9 µg/kg to approximately 1200.0 µg/kg, approximately 31.0 µg/kg to approximately 1000.0 µg/kg, approximately 31.5 µg/kg to approximately 950.0 µg/kg, approximately 32.0 µg/kg to approximately 900.0 µg/kg, approximately 32.5 µg/kg to approximately 850.0 µg/kg, approximately 33.0 µg/kg to approximately 800.0 µg/kg, approximately 33.5 µg/kg to approximately 750.0 µg/kg, approximately 34.0 µg/kg to approximately 700.0 µg/kg, approximately 34.5 µg/kg to approximately 650.0 µg/kg, approximately 35.0 µg/kg to approximately 600.0 µg/kg, approximately 35.5 µg/kg to approximately 550.0 µg/kg, approximately 36.0 µg/kg to approximately 500.0 µg/kg, approximately 36.5 µg/kg to approximately 490.0 µg/kg, approximately 37.0 µg/kg to approximately 480.0 µg/kg, approximately 37.5 µg/kg to approximately 470.0 µg/kg, approximately 38.0 µg/kg to approximately 460.0 µg/kg, approximately 38.5 µg/kg to approximately 450.0 µg/kg, approximately 39.0 µg/kg to approximately 440.0 µg/kg, approximately 39.5 µg/kg to approximately 430.0 µg/kg, approximately 40.0 µg/kg to approximately 420.0 µg/kg, approximately 41.0 µg/kg to approximately 410.0 µg/kg, approximately 42.0 µg/kg to approximately 400.0 µg/kg, approximately 43.0 µg/kg to approximately 390.0 µg/kg, approximately 44.0 µg/kg to approximately 380.0 µg/kg, approximately 45.0 µg/kg to approximately 370.0 µg/kg, approximately 46.0 µg/kg to approximately 360.0 µg/kg, approximately 47.0 µg/kg to approximately 350.0 µg/kg, approximately 48.0 µg/kg to approximately 340.0 µg/kg, approximately 49.0 µg/kg to approximately 330.0 µg/kg, approximately 50.0 µg/kg to approximately 320.0 µg/kg, approximately 55.0 µg/kg to approximately 310.0 µg/kg, approximately 60.0 µg/kg to approximately 300.0 µg/kg, approximately 65.0 µg/kg to approximately 290.0 µg/kg, approximately 70.0 µg/kg to approximately 280.0 µg/kg, approximately 75.0 µg/kg to approximately 270.0 µg/kg, approximately 80.0 µg/kg to approximately 260.0 µg/kg, approximately 85.0 µg/kg to approximately 250.0 µg/kg, approximately 90.0 µg/kg to approximately 240.0 µg/kg, approximately 95.0 µg/kg to approximately 230.0 µg/kg, approximately 100.0 µg/kg to approximately 220.0 µg/kg, approximately 110.0 µg/kg to approximately 210.0 µg/kg, approximately 120.0 µg/kg to approximately 200.0 µg/kg, approximately 130.0 µg/kg to approximately 190.0 µg/kg, approximately 140.0 µg/kg to approximately 180.0 µg/kg, and approximately 150.0 µg/kg to approximately 170.0 µg/kg.

In one embodiment, the diagnostic effective amount of the compound of Formula 1 is in the range from approximately 3000.0 µg/kg to approximately 1500.0 µg/kg.

In one embodiment, the diagnostic effective amount of the compound of Formula 1 is in the range from approximately 1500.0 µg/kg to approximately 1000.0 µg/kg.

In one embodiment, the diagnostic effective amount of the compound of Formula 1 is in the range from approximately 1000.0 µg/kg to approximately 500.0 µg/kg.

In one embodiment, the diagnostic effective amount of the compound of Formula 1 is in the range from approximately 500.0 µg/kg to approximately 170.0 µg/kg.

In one embodiment, the diagnostic effective amount of the compound of Formula 1 is in the range from approximately 170.0 µg/kg to approximately 120.0 µg/kg.

In one embodiment, the diagnostic effective amount of the compound of Formula 1 is in the range from approximately 120.0 µg/kg to approximately 60.0 µg/kg.

In one embodiment, the diagnostic effective amount of the compound of Formula 1 is in the range from approximately 30.0 µg/kg to approximately 500.0 µg/kg.

In one embodiment, the diagnostic effective amount of the compound of Formula 2 is in the range from approximately 3000.0 µg/kg to approximately 1500.0 µg/kg.

In one embodiment, the diagnostic effective amount of the compound of Formula 2 is in the range from approximately 1500.0 µg/kg to approximately 1000.0 µg/kg.

In one embodiment, the diagnostic effective amount of the compound of Formula 2 is in the range from approximately 1000.0 µg/kg to approximately 500.0 µg/kg.

In one embodiment, the diagnostic effective amount of the compound of Formula 2 is in the range from approximately 500.0 µg/kg to approximately 170.0 µg/kg.

In one embodiment, the diagnostic effective amount of the compound of Formula 2 is in the range from approximately 170.0 µg/kg to approximately 120.0 µg/kg.

In one embodiment, the diagnostic effective amount of the compound of Formula 2 is in the range from approximately 120.0 µg/kg to approximately 60.0 µg/kg.

In one embodiment, the diagnostic effective amount of the compound of Formula 2 is in the range from approximately 30.0 µg/kg to approximately 500.0 µg/kg.

The diagnostic effective amount of each of the compound of Formula 1 and the compound of Formula 2 according to the invention is effective over a wide dosage range. The exact dosage will depend upon the route of administration, the form in which each compound is administered, the gender, age, and body weight of the subject to be treated, and the preference and experience of the administrator.

In selected embodiments, the fluorescence intensity of each of the administered compound of Formula 1 and the administered compound of Formula 2 may be independently measured at a time period of, for example, less than 24 hrs, 23 hrs, 22 hrs, 21 hrs, 20 hrs, 19 hrs, 18 hrs, 17 hrs, 16 hrs, 15 hrs, 14 hrs, 13 hrs, 12 hrs, 11 hrs, 10 hrs, 9.5 hrs, 9.0 hrs, 8.5 hrs, 8.0 hrs, 7.5 hrs, 7.0 hrs, 6.5 hrs, 6.0 hrs, 5.5 hrs, 5.0 hrs, 4.75 hrs, 4.50 hrs, 4.25 hrs, 4.00 hrs, 3.75 hrs, 3.50 hrs, 3.25 hrs, 3.00 hrs, 2.75 hrs, 2.50 hrs, 2.25 hrs, 2.00 hrs, 1.75 hrs, 1.50 hrs, 1.25 hrs, 1.00 hrs, 0.90 hrs, 0.80 hrs, 0.70 hrs, 0.60 hrs, 0.50 hrs, 0.40 hrs, 0.30 hrs, 0.20 hrs after administering.

In selected embodiments, the fluorescence intensity of each of the administered compound of Formula 1 and the administered compound of Formula 2 may be independently measured at a time period of, for example, greater than 23 hrs, 22 hrs, 21 hrs, 20 hrs, 19 hrs, 18 hrs, 17 hrs, 16 hrs, 15 hrs, 14 hrs, 13 hrs, 12 hrs, 11 hrs, 10 hrs, 9.5 hrs, 9.0 hrs, 8.5 hrs, 8.0 hrs, 7.5 hrs, 7.0 hrs, 6.5 hrs, 6.0 hrs, 5.5 hrs, 5.0 hrs, 4.75 hrs, 4.50 hrs, 4.25 hrs, 4.00 hrs, 3.75 hrs, 3.50 hrs, 3.25 hrs, 3.00 hrs, 2.75 hrs, 2.50 hrs, 2.25 hrs, 2.00 hrs, 1.75 hrs, 1.50 hrs, 1.25 hrs, 1.00 hrs, 0.90 hrs, 0.80 hrs, 0.70 hrs, 0.60 hrs, 0.50 hrs, 0.40 hrs, 0.30 hrs, 0.20 hrs, 0.10 hrs after administering.

In selected embodiments, the fluorescence intensity of each of the administered compound of Formula 1 and the administered compound of Formula 2 may be independently measured at a time period in the range from approximately 0.10 hrs to approximately 24 hrs, approximately 0.20 hrs to approximately 23 hrs, approximately 0.30 hrs to approximately 22 hrs, approximately 0.40 hrs to approximately 21 hrs, approximately 0.50 hrs to approximately 20 hrs, approximately 0.60 hrs to approximately 19 hrs, approximately 0.70 hrs to approximately 18 hrs, approximately 0.80 hrs to approximately 17 hrs, approximately 0.90 hrs to approximately 16 hrs, approximately 1.00 hr to approximately 15 hrs, approximately 1.25 hrs to approximately 14 hrs, approximately 1.50 hrs to approximately 13 hrs, approximately 1.75 hrs to approximately 12 hrs, approximately 2.00 hrs to approximately 11 hrs, approximately 2.25 hrs to approximately 10 hrs, approximately 2.50 hrs to approximately 9.5 hrs, approximately 2.75 hrs to approximately 9.0 hrs, approximately 3.00 hrs to approximately 8.5 hrs, approximately 3.25 hrs to approximately 8.0 hrs, approximately 3.50 hrs to approximately 7.5 hrs, approximately 3.75 hrs to approximately 7.0 hrs, approximately 4.00 hrs to approximately 6.5 hrs, approximately 4.25 hrs to approximately 6.0 hrs, approximately 4.50 hrs to approximately 5.5 hrs, approximately 4.75 hrs to approximately 5.0 hrs after administering.

In the embodiments of the methods described herein, the sample is illuminated with a wavelength of light selected to give a detectable optical response, and observed with a means for detecting the optical response. Equipment that is useful for illuminating the dye compounds of the invention includes, but is not limited to, tungsten lamps, hand-held ultraviolet lamps, mercury arc lamps, xenon lamps, light emitting diodes (LED), lasers and laser diodes. These illumination sources are optionally integrated into surgical cameras, laparoscopes and microscopes. Preferred embodiments of the invention are dyes that are excitable at or near the wavelengths 633-636 nm, 647 nm, 660 nm, 680 nm and beyond 700 nm, such as 780 nm, 810 nm and 850 nm as these regions closely match the output of relatively inexpensive excitation sources. The optical response is optionally detected by visual inspection, or by use of any of the following devices: CCD cameras, video cameras, photographic film.

The NIR imaging probe used was the compound of Formula 1; excitation 773 nm and emission 790 nm or independently, Formula 2, excitation 772 nm and emission 787 nm.

The compound of Formula 1 and the compound of Formula 2 as described herein can be administered in a manner compatible with the dosage formulation, and in such amount as will be effective or suitable for in vivo imaging. The quantity to be administered depends on a variety of factors including, e.g., the age, body weight, physical activity, and diet of the individual, the tissue or organ to be imaged, and type of procedure or surgery to be performed. In certain embodiments, the size of the dose may also be determined by the existence, nature, and extent of any adverse side effects that accompany the administration of the compound in a particular individual.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose may take the form of solid, semi-solid, or lyophilized powder forms, preferably in unit dosage forms suitable for simple administration of precise dosages. In some embodiments, the dose is provided in a container, vial or syringe at a particular dosage for one or more administrations.

As used herein, the term "unit dosage form" refers to physically discrete units suitable as unitary dosages for humans and other mammals, each unit containing a predetermined quantity of an imaging agent calculated to produce the desired onset, tolerability, and/or fluorescent effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the imaging agent.

Methods for preparing such dosage forms are known to those skilled in the art (see, e.g., REMINGTON'S PHARMACEUTICAL SCIENCES, 18th ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMAMCEUTICAL SCIENCES, 18th ED., Mack Publishing Co., Easton, Pa. (1990)).

In certain embodiments, the dosage forms contain a stabilizing agent for the storage, isolation, purification, and/or lyophilization of the compounds. Agents for lyophilization include, but are not limited to, a saccharide such as a monosaccharide, a disaccharide or dextran. Other saccharides include glucose, galactose, xylose, glucuronic acid, trehalose, dextran, hydroxyethyl starch, mannitol, or 5% dextrose.

For parenteral administration, e.g., intravenous injection, intra-arterial injection, subcutaneous injection, intramuscular injection and the like, the effective dose can be in the form of sterile injectable solutions and sterile packaged powders. Preferably, injectable solutions are formulated at a pH of from about 4.5 to about 7.5, or physiological pH.

In some embodiments, the effective dose for imaging contains a lyophilized compound described herein in a high-quality, easily dissolved form which is stable for months at room temperature. The lyophilized compound of Formula 1 or Formula 2 can be stored in any suitable type of sealed container, such as a sealed vial or syringe that contains an amount of the compound for a single dosage for a subject, such as a human adult. The term "vial" is used broadly herein, to refer to any drug-packaging device that is designed and suitable for sealed and sterile storage, shipping, and handling of small (e.g., single-dosage) quantities of drugs. Single-chamber vials (which would contain only the lyophilized compound, with no water) are well known; a typical single-chamber vial may be designed for use with an intravenous infusion bag. Alternatively, two-chamber vials can be used that contain both the lyophilized compound and a sterile aqueous solution, to enable immediate reconstitution and injection of an aqueous liquid containing the compound of Formula 1 or Formula 2.

Provided herein are kits containing a compound of Formula 1 or a compound of Formula 2. In some embodiments, a kit comprises one or more vials or syringes containing compound of Formula 1 in, for example, a lyophilized form.

In other embodiments, a kit comprises one or more vials or syringes containing compound of Formula 2 in, for example, a lyophilized form. Such kits can also include a pharmaceutically acceptable carrier or a sterile aqueous solution, e.g., sterile water for reconstituting the compound prior to administration. In some cases, the kit also includes a sterile syringe for parenteral administration of the compound or for use with an intravenous infusion bag. The kit can also include an instruction manual for use.

When ranges are used herein, all combinations and subcombinations of ranges and specific embodiments therein are intended to be included. Use of the term "approximately" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments that "consist of" or "consist essentially of" the described features.

III. Examples

Example 1

The compound of Formula 1 may be synthesized by dissolving 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide, innersalt, trisodium salt (1 g, 1.05 mmol) in 25 mL of water and sparging with nitrogen for 15 minutes. Sodium 4-hydroxybenzenesulfonate dihydrate (875 mg, 3.77 mmol) was dissolved in 3.6 mL 1N NaOH (3.6 mmol) and added to the reaction mixture. The reaction mixture was placed in an oil bath at 40° C. and stirred for 16 hours. The solution was dried by rotary evaporation and the product was then recrystallized from 80:20 ethanol:water. The compound was filtered then washed with ethanol and dried under vacuum at 60° C. for 18 hours.

The polymorph of the compound of Formula 1 (Form A) can be prepared as follows:

A mixture of 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide, innersalt, trisodium salt (20 g, 21 mmol) and Sodium 4-hydroxybenzenesulfonate dihydrate (5.84 g, 25.2 mmol) is suspended in water (120 ml). The suspension is heated to 85° C. where complete dissolution is observed. Aqueous sodium hydroxide (10N, 2.5 ml, 25 mmol) is added dropwise and the reaction stirred for 45 min. Isopropanol (360 ml) is added slowly to maintain the reaction temperature above 60° C. The mixture is then slowly cooled to ambient temperature and the resulting slurry filtered. The filter cake is rinsed with 40 ml isopropanol:water (3:1) and twice with 40 ml isopropanol and dried at 50-60° C. under vacuum to obtain 18.4 g of the compound of Formula 1 as a dark green solid. Ten grams (9 mmol) of this material is then recrystallized by dissolving in water (50 ml) and isopropanol (100 ml) at approximately 70° C., and slowly cooling the mixture to ambient temperature. The solids are collected by filtration and rinsed with 20 ml isopropanol:water (2:1) and twice with 20 ml isopropanol and dried at 50-60° C. under vacuum to obtain 6.7 g of the compound Formula 1 as a crystalline dark green solid.

X-Ray Powder Diffraction (XRPD) for Form A

XRPD analysis was carried out on a PANalytical X'pert pro, scanning the samples between 3 and 35° 2θ. The material was gently ground and loaded onto a multiwell plate with Kapton or mylar polymer film to support the sample. The multiwell plate was then loaded into a Panalytical diffractometer running in transmission mode and analyzed.

Figure 1B:
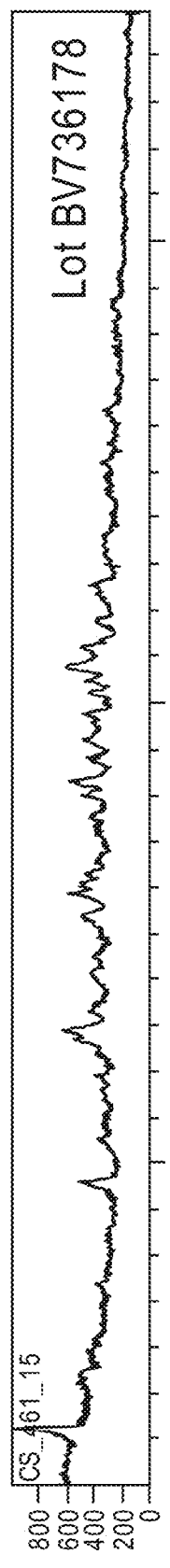
Figure 1C:
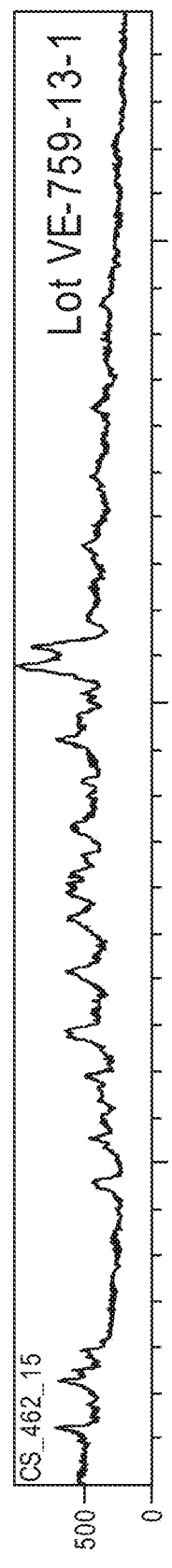
Figure 1D:
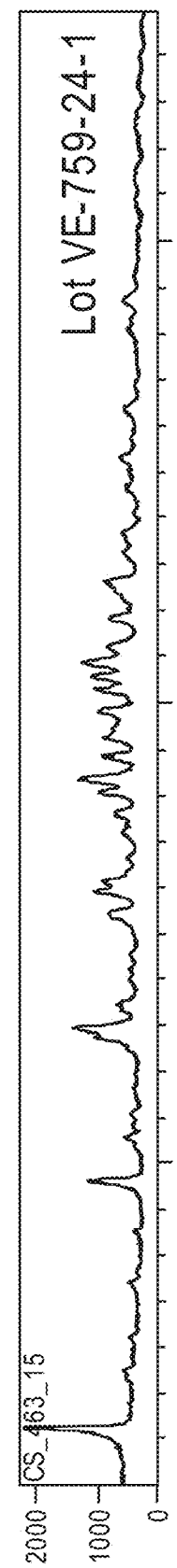
Figure 1E:
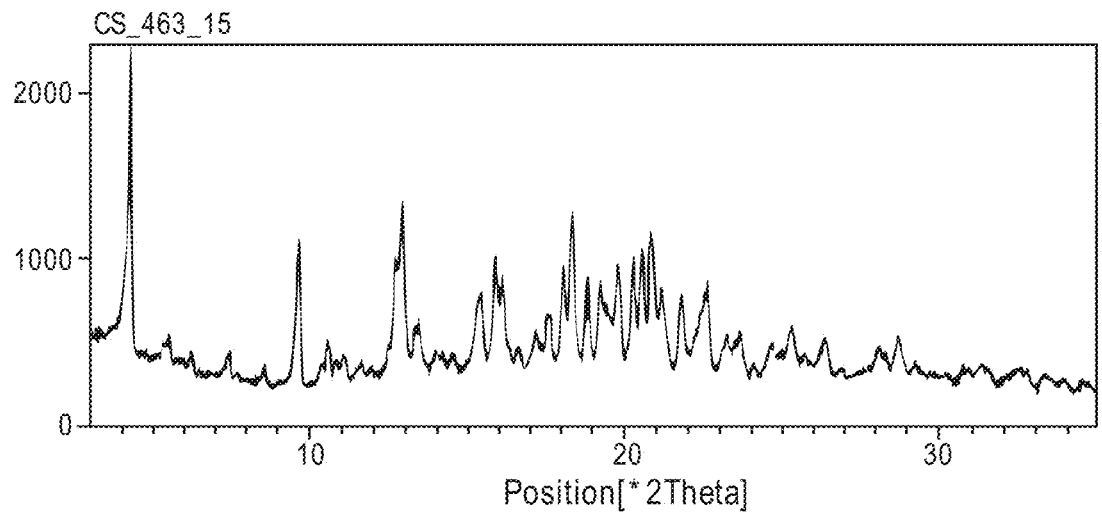

The XRPD data are shown in FIG. 1A-1F. As illustrated, FIGS. 1A and 1C are identical and are both moderately crystalline and represent Form A. FIG. 1B is similar in crystallinity and is Form A.

FIG. 1D is crystalline. FIG. 1E is an enlargment of FIG. 1D. FIG. 1D and FIG. 1E represent Form A.

Figure 1F:
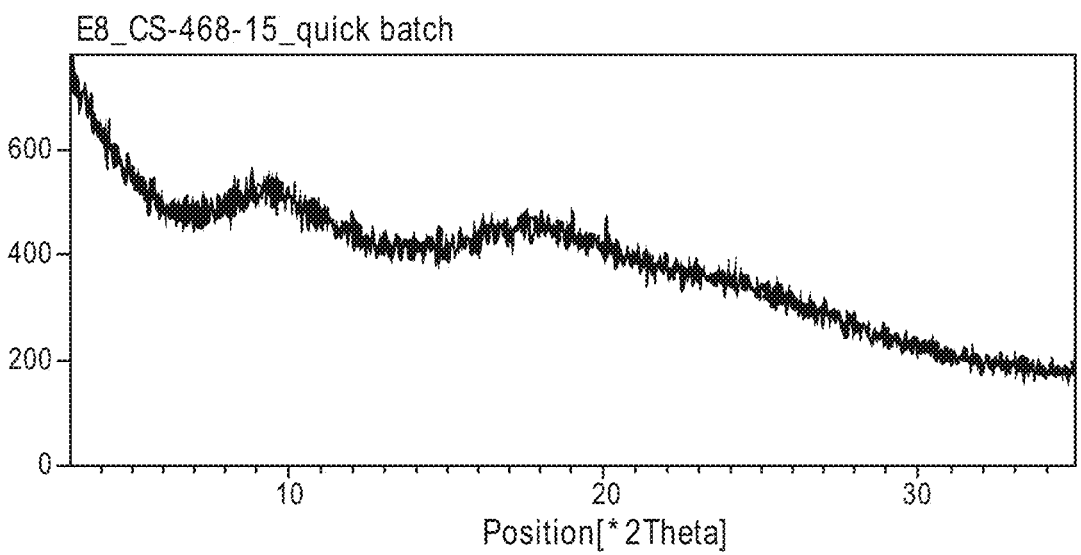

FIG. 1F is the amorphous form.

Characteristic XRPD angles and d-spacings for the solid state form are summarized in Table 1 for Form A. Peak positions were measured and tabulated.

TABLE 1

Peak Data of IRDye 800BK Lot: BV736185 (FIG. 1A) XPRD Analysis

| Pos. [° 2Th.] | Height [cts] | FWHM [° 2Th.] | d-spacing [Å] | Rel. Int. [%] |
|---|---|---|---|---|
| 4.2384 | 362.12 | 0.1279 | 20.84818 | 29.2 |
| 5.2771 | 550.29 | 0.0895 | 16.74659 | 44.37 |
| 5.4888 | 295.59 | 0.0768 | 16.10118 | 23.83 |
| 5.9607 | 293.22 | 0.0512 | 14.82759 | 23.64 |
| 9.5414 | 221.36 | 0.1535 | 9.26957 | 17.85 |
| 10.5728 | 314.69 | 0.0768 | 8.36752 | 25.37 |
| 10.9522 | 224.35 | 0.1023 | 8.07854 | 18.09 |
| 11.3914 | 371.25 | 0.0768 | 7.76803 | 29.93 |
| 11.9362 | 322.74 | 0.0768 | 7.41466 | 26.02 |
| 12.8323 | 579.36 | 0.0895 | 6.89882 | 46.71 |
| 14.1854 | 785.5 | 0.1279 | 6.24366 | 63.33 |
| 15.0743 | 305.87 | 0.1279 | 5.87743 | 24.66 |
| 15.3653 | 384.4 | 0.1279 | 5.76676 | 30.99 |
| 15.5532 | 262.25 | 0.1023 | 5.69752 | 21.15 |
| 15.8747 | 444.26 | 0.0512 | 5.58284 | 35.82 |
| 16.3152 | 405.54 | 0.1535 | 5.43308 | 32.7 |
| 16.7216 | 378.51 | 0.0768 | 5.30195 | 30.52 |
| 17.3776 | 514.77 | 0.064 | 5.10327 | 41.51 |
| 18.2698 | 226.8 | 0.1023 | 4.856 | 18.29 |
| 19.1518 | 465.59 | 0.1535 | 4.63431 | 37.54 |
| 19.5492 | 393.65 | 0.1279 | 4.54099 | 31.74 |
| 20.1805 | 277.83 | 0.1023 | 4.40035 | 22.4 |
| 20.7531 | 1146.9 | 0.1151 | 4.2802 | 92.47 |
| 21.2128 | 1240.24 | 0.1151 | 4.18848 | 100 |
| 21.8521 | 229.87 | 0.2047 | 4.06738 | 18.53 |
| 22.6123 | 239.17 | 0.1535 | 3.93232 | 19.28 |
| 23.389 | 331.71 | 0.064 | 3.80346 | 26.75 |
| 23.8748 | 148.63 | 0.1535 | 3.72716 | 11.98 |
| 24.3664 | 124.78 | 0.1535 | 3.65307 | 10.06 |
| 24.9407 | 221.2 | 0.1279 | 3.57024 | 17.84 |
| 26.4158 | 297.98 | 0.1279 | 3.37412 | 24.03 |
| 28.658 | 136.22 | 0.1791 | 3.11503 | 10.98 |

Characteristic XRPD angles and d-spacings for the solid state form are summarized in Table 2 for Form A. Peak positions were measured and tabulated.

TABLE 2

Peak data of IRDye 800BK Lot: VE-759-24-1 (FIG. 1E) XRPD Analysis

| Pos. [° 2Th.] | Height [cts] | FWHM [° 2Th.] | d-spacing [Å] | Rel. Int. [%] |
|---|---|---|---|---|
| 4.272 | 1845.05 | 0.064 | 20.68408 | 100 |
| 9.6191 | 863.9 | 0.0895 | 9.19491 | 46.82 |
| 10.5611 | 267.84 | 0.1023 | 8.37677 | 14.52 |
| 12.4823 | 217.24 | 0.0768 | 7.09145 | 11.77 |
| 12.7274 | 748.04 | 0.0895 | 6.95545 | 40.54 |
| 12.93 | 1108.7 | 0.0768 | 6.84692 | 60.09 |
| 13.4567 | 353.68 | 0.1279 | 6.58007 | 19.17 |
| 14.197 | 188.01 | 0.1023 | 6.23861 | 10.19 |
| 15.4372 | 537.33 | 0.064 | 5.74009 | 29.12 |
| 15.8734 | 703.35 | 0.0384 | 5.58329 | 38.12 |
| 16.1055 | 637.51 | 0.064 | 5.50336 | 34.55 |
| 16.6046 | 222 | 0.1279 | 5.33906 | 12.03 |
| 17.1929 | 293.61 | 0.1023 | 5.15766 | 15.91 |
| 17.559 | 419.11 | 0.1023 | 5.05094 | 22.72 |
| 18.0101 | 705.32 | 0.1023 | 4.92543 | 38.23 |
| 18.2864 | 1035.04 | 0.1663 | 4.85163 | 56.1 |
| 18.7831 | 635.82 | 0.0512 | 4.72445 | 34.46 |
| 19.1781 | 617.24 | 0.0895 | 4.62801 | 33.45 |
| 19.4323 | 420.97 | 0.4093 | 4.56805 | 22.82 |
| 19.7836 | 680.51 | 0.064 | 4.48772 | 36.88 |
| 20.2392 | 744.22 | 0.0512 | 4.38771 | 40.34 |
| 20.5039 | 801.47 | 0.1151 | 4.33166 | 43.44 |
| 20.8076 | 960.22 | 0.1407 | 4.26912 | 52.04 |
| 21.1497 | 546.41 | 0.1791 | 4.20083 | 29.61 |
| 21.7763 | 541.2 | 0.064 | 4.08136 | 29.33 |
| 22.5703 | 573.98 | 0.0512 | 3.93954 | 31.11 |
| 23.1948 | 292.69 | 0.1023 | 3.83487 | 15.86 |
| 23.6245 | 311.01 | 0.1279 | 3.76608 | 16.86 |
| 24.6218 | 243.08 | 0.1535 | 3.61575 | 13.17 |
| 25.2623 | 343.69 | 0.1791 | 3.52551 | 18.63 |
| 26.3234 | 274.93 | 0.1791 | 3.38575 | 14.9 |
| 28.0536 | 225.6 | 0.1535 | 3.18075 | 12.23 |
| 28.6694 | 301.22 | 0.2047 | 3.11382 | 16.33 |

In one embodiment, it is possible to make Form B from Form A. Form A is crystalline and exists as small birefringent particles with no defined morphology. The material is hygroscopic (27 wt % uptake up-to 90% RH) and can change form under stress conditions. A form change does occur when Form A is subjected to 40° C./75% RH. This form corresponds with the form found with the post-GVS sample. HPLC purity showed no change.

FIG. 1H and FIG. 1I represent Form B. For comparison, FIG. 1G is identical to FIG. 1D.

Characteristic XRPD angles and d-spacings for the solid state form are summarized in Table 3 for Form B. Peak positions were measured and tabulated.

TABLE 3

Peak data of IRDye 800BK Lot: VE-759-24-1 Form B XRPD Analysis

| Pos. [° 2Th.] | Height [cts] | FWHM [° 2Th.] | d-spacing [Å] | Rel. Int. [%] |
|---|---|---|---|---|
| 5.2989 | 1193.55 | 0.064 | 16.67783 | 52.81 |
| 5.9816 | 649.44 | 0.0512 | 14.77594 | 28.74 |
| 9.535 | 387.23 | 0.064 | 9.27578 | 17.13 |
| 10.6007 | 690.31 | 0.1023 | 8.3456 | 30.55 |
| 10.9387 | 376.49 | 0.0895 | 8.08848 | 16.66 |
| 11.3924 | 413.39 | 0.064 | 7.76734 | 18.29 |
| 11.9715 | 817.54 | 0.0768 | 7.39285 | 36.18 |
| 12.8677 | 587.96 | 0.1279 | 6.8799 | 26.02 |
| 14.2153 | 1273.22 | 0.0936 | 6.22544 | 56.34 |
| 14.2827 | 1000.8 | 0.078 | 6.21161 | 44.28 |
| 15.9468 | 606.88 | 0.2496 | 5.55317 | 26.85 |
| 16.3781 | 600.12 | 0.1092 | 5.4079 | 26.55 |
| 16.7597 | 562.34 | 0.1092 | 5.28561 | 24.88 |

TABLE 3-continued

Peak data of IRDye 800BK Lot: VE-759-24-1 Form B XRPD Analysis

| Pos. [° 2Th.] | Height [cts] | FWHM [° 2Th.] | d-spacing [Å] | Rel. Int. [%] |
|---|---|---|---|---|
| 17.3714 | 797.24 | 0.078 | 5.10083 | 35.28 |
| 17.7698 | 277.37 | 0.1872 | 4.98736 | 12.27 |
| 18.4312 | 246.4 | 0.156 | 4.80986 | 10.9 |
| 18.6816 | 475.06 | 0.1872 | 4.74595 | 21.02 |
| 19.1392 | 766.24 | 0.078 | 4.63351 | 33.91 |
| 19.5987 | 600.29 | 0.0936 | 4.52589 | 26.56 |
| 20.1626 | 509.11 | 0.0624 | 4.40057 | 22.53 |
| 20.7073 | 1255.16 | 0.1404 | 4.28603 | 55.54 |
| 21.2464 | 2259.95 | 0.1092 | 4.17848 | 100 |
| 21.8382 | 456.8 | 0.156 | 4.06656 | 20.21 |
| 22.6653 | 385.85 | 0.1872 | 3.92 | 17.07 |
| 23.4295 | 644.04 | 0.2808 | 3.79383 | 28.5 |
| 23.9381 | 351.56 | 0.1872 | 3.71438 | 15.56 |
| 24.9551 | 451.86 | 0.2184 | 3.56525 | 19.99 |
| 26.4745 | 574.6 | 0.0468 | 3.36399 | 25.43 |

Example 2

The compound of Formula 2 may be synthesized by dissolving 3,3-Dimethyl-2-[2-[2-chloro-3-[2-[1,3-dihydro-3,3-dimethyl-5-sulfo-1-(4-sulfobutyl)-2H-indol-2-ylidene]-ethylidene]-1-cyclohexen-1-yl]-ethenyl]-5-sulfo-1-(4-sulfobutyl)-3H-indolium hydroxide, innersalt, trisodium salt (1 g, 1.05 mmol) in 25 mL of water and sparging with nitrogen for 15 minutes. Sodium phenoxide trihydrate (390 mg, 2.29 mmol) was dissolved in 2 mL ultrapure water and added to the reaction mixture. The reaction mixture was placed in an oil bath at 40° C. and stirred for 4 hours. The solution was dried by rotary evaporation and the product was then recrystallized from 90:10 ethanol:water. The compound was filtered then washed with ethanol and dried under vacuum at 60° C. for 18 hours.

Comparative Example 1

The structure of the compound of comparative example 1, also referred to as 800CW, is shown below:

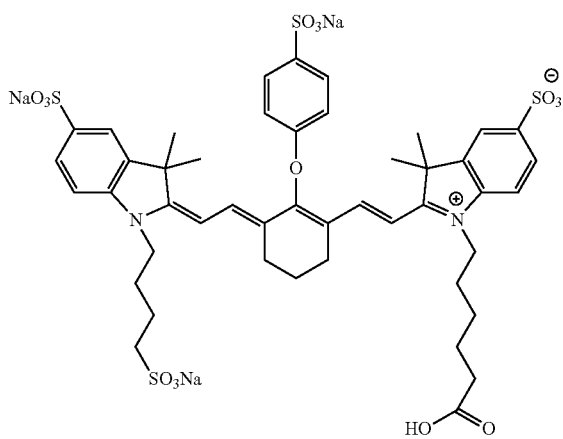

The structure of indocyanine green (ICG) dye is shown below:

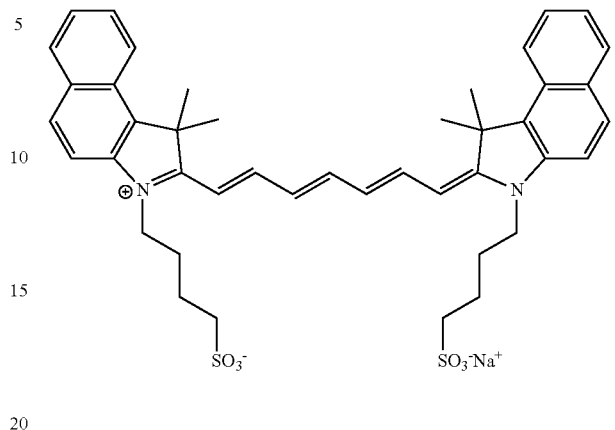

Example 3: In Vitro

Figure 2A:
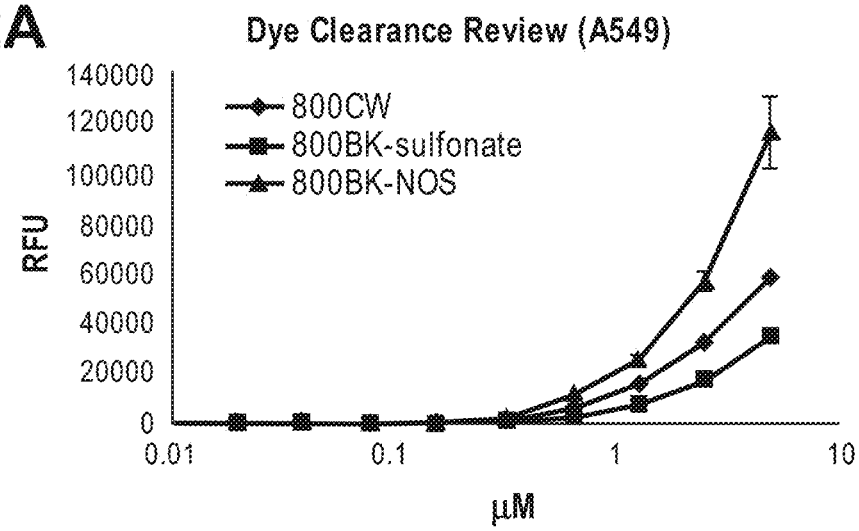
FIGS. 2A, and 2B illustrate in vitro cell-based analyses for A549 cells (A) and A431 cells (B).
Figure 2B:
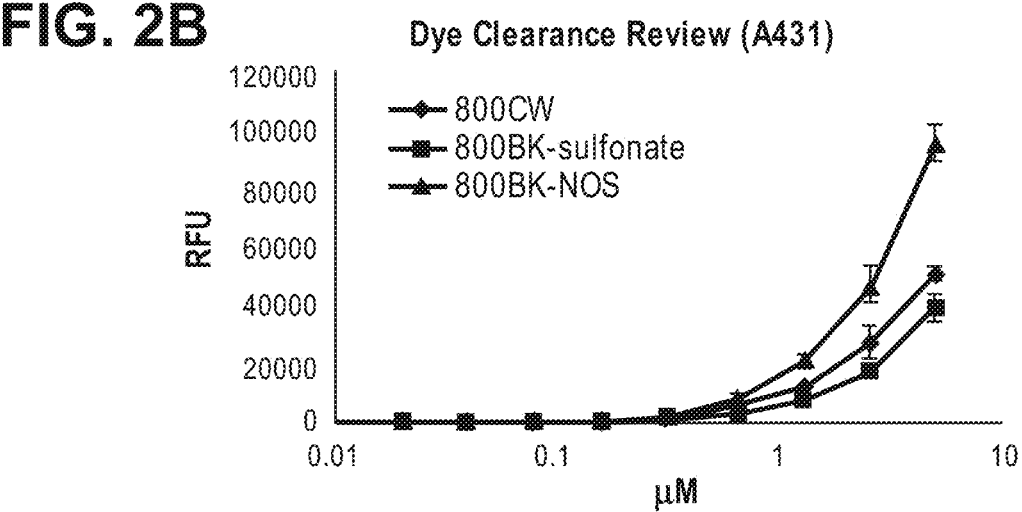
Figure 2C:
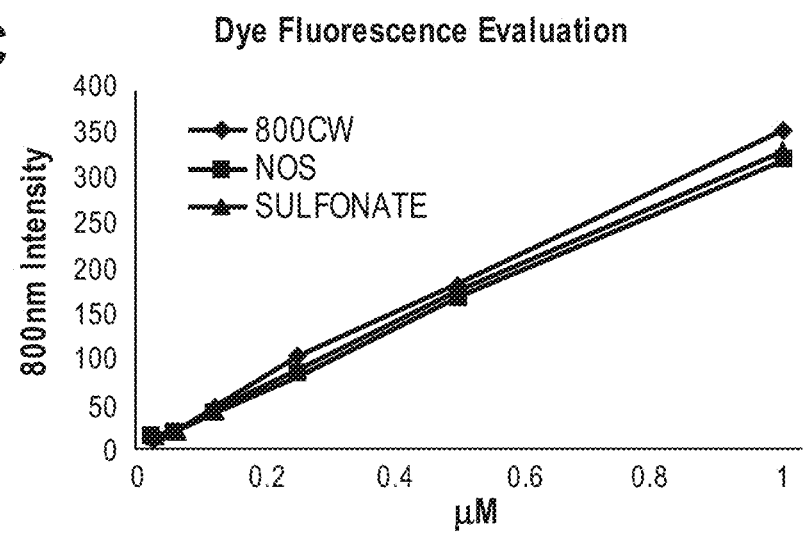
FIG. 2C shows fluorescence as a function of concentration of each dye prepared for in vivo imaging (0.03-1 µM).

In vitro cell-based assays with two carcinoma cell lines (A431 and A549) were done to assess non-specific binding of the compound of Formula 1 and the compound of Formula 2. The dyes were compared to 800CW. This is shown in FIGS. 2A, 2B, and 2C.

The compound of Formula 2 demonstrated a significant increase in non-specific binding compared to either the compound of Formula 1 and 800CW by two-fold. The compound of Formula 1 was more comparable to 800CW.

To confirm all three compounds have comparable fluorescence, a dilution series was made and imaged on an Odyssey SA fluorescence imaging system (LI-COR Biosciences). The fluorescence in each well was quantified with the instrument software. FIG. 2C shows that all three compounds in this test were very close in fluorescence, thus confirming that the increased fluorescence at higher concentrations noted in plate-based assay is likely due to a tendency of the compound to bind non-specifically to cells.

In general, low non-specific binding is an advantage. Both cell lines show low non-specific binding for all compounds at concentrations below 1 μM. However all begin to show some binding at higher concentrations.

Example 4: In Vivo

Animals injected with the probes were imaged over time using the 800 fluorescence channel of the Pearl Impulse Imaging System (LI-COR Biosciences). Clearance profiles for 800CW, the compound of Formula 1, and the compound of Formula 2 were carried out in nude mice (dose of 1 nmole for all compounds). Serial images and excised organs were evaluated over a 24 hr period. Dorsal image series are presented in FIG. 3. A Pearl Impulse small animal imaging system was used for all animal and organ image acquisitions.

The compound of comparative example 1 is used as the reference. From the Dorsal view there is no kidney signal for any probe. At 2 hrs post injection, the compound of Formula 2 exhibits high signal, emanating in the liver region visible from the back. The compound of Formula 2 never fully disseminates because it is collected rapidly in the liver and by 5 hr post injection, the whole body signal is low compared to 800CW and the compound of Formula 1.

Example 5: Ventral Images

Ventral images are presented in FIG. 4. From visual examination, the compound of Formula 1 and 800CW are similar in their clearance pattern. These two probes appear to clear rapidly via the kidney. This feature is very useful for imaging the urinary system.

The compound of Formula 2, on the other hand, clears through the liver. This feature is a very useful attribute for a biliary duct monitoring dye which may "mimic" ICG that is currently used for this clinical application. From the in vitro plate-based assays it appeared both the compound of Formula 1 and the compound of Formula 2 have similar fluorescence intensities to 800CW. However, from the in vivo data, it appeared that the compound of Formula 1 moves rapidly through the tissues but is retained for an extended period in organs.

Bladder signal is the strongest signal noted for 800CW and the compound of Formula 1 probes (purple arrows).

Figure 5:
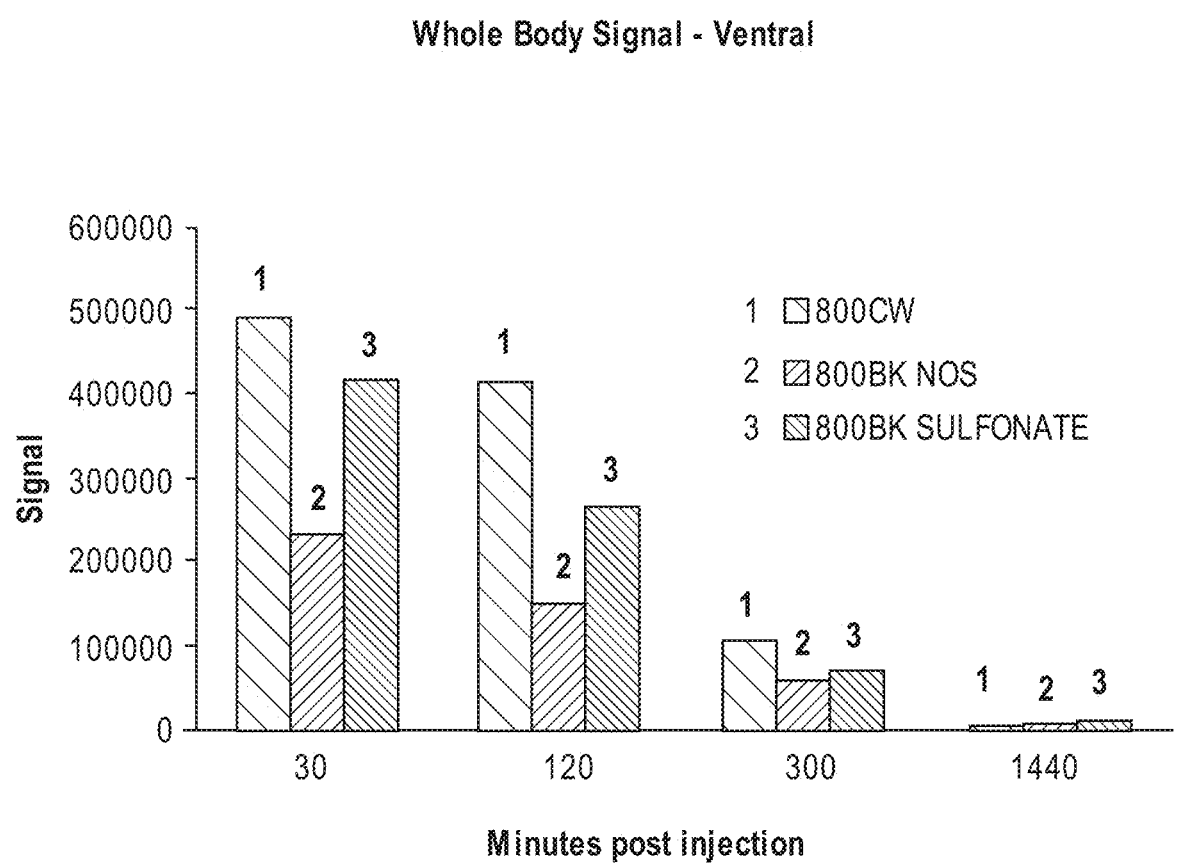
FIG. 5 illustrates whole body fluorescence intensity numbers for the images of FIG. 4 for the compound of comparative example 1, the compound of Formula 1, and the compound of Formula 2 probes.

Whole body fluorescence numbers for the three probes (ventral view) are shown in FIG. 5. Non-invasive imaging will not capture signals for the full depth of the animal but the intensity values are useful to show a relative trend.

There is a slower clearance for 800CW and the compound of Formula 1 as compared to the compound of Formula 2. The signal for the compound of Formula 2 appears to be lower overall than the signal for 800CW and the compound of Formula 1, however, it appears to rapidly collect in the liver. At 24 hrs post administration, the remaining fluorescence is diminished for all three probes to roughly the same extent.

Another way of examining fluorescence signals is by measuring the % of the compound remaining at a particular time point. The 30 min time point is the baseline to which other time points are normalized. This data are presented below in Table 4.

|  | 30 min | 120 min | 300 min | 1440 min |
|---|---|---|---|---|
| Compound of comparative example 1 (800CW) | 100 | 85 | 23 | 0.8 |
| Compound of Formula 1 (800BK-sulfonate) | 100 | 81 | 19 | 1.4 |
| Compound of Formula 2 (800BK-NOS) | 100 | 70 | 14 | 1.4 |

The percent signal remaining at each time is shown with the 30 min time point post-injection, which is used as the baseline.

The greatest reduction occurs for the compound of Formula 2 at 2 hrs. The compound of Formula 1 is very similar to 800CW and by 24 hrs post injection, all compounds are very similar in remaining signals at less than 2% of baseline.

Example 5: Organs

Figure 6D:
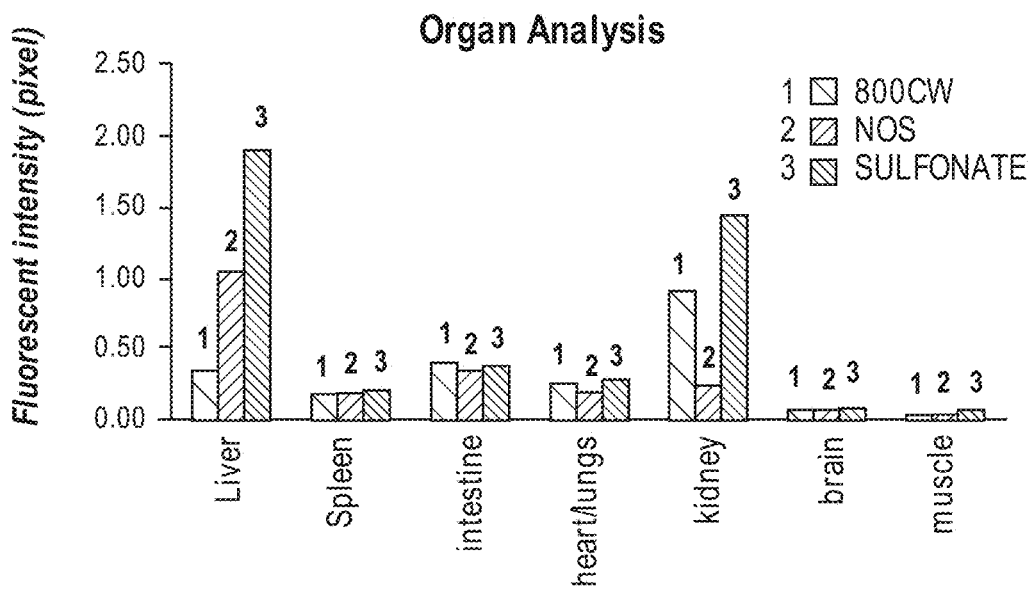

Organs were excised at 24 hrs and imaged. Data is presented in FIG. 6.

The compound of Formula 1 is retained at higher levels in the liver and kidney compared to the compound of Formula 2 at 24 hrs post injection. Surprisingly, the compound of Formula 2, which clears predominantly from the liver, has lower liver signals at 24 hrs when compared to 800CW and the compound of Formula 1. This may be explained by a slower overall clearance from tissue for the compound of Formula 1 as compared to 800CW and the compound of Formula 2.

None of 800CW or the compound of Formula 1 or the compound of Formula 2 is detected in the brain and is likely due to their inability to cross the blood brain barrier.

Figure 7:
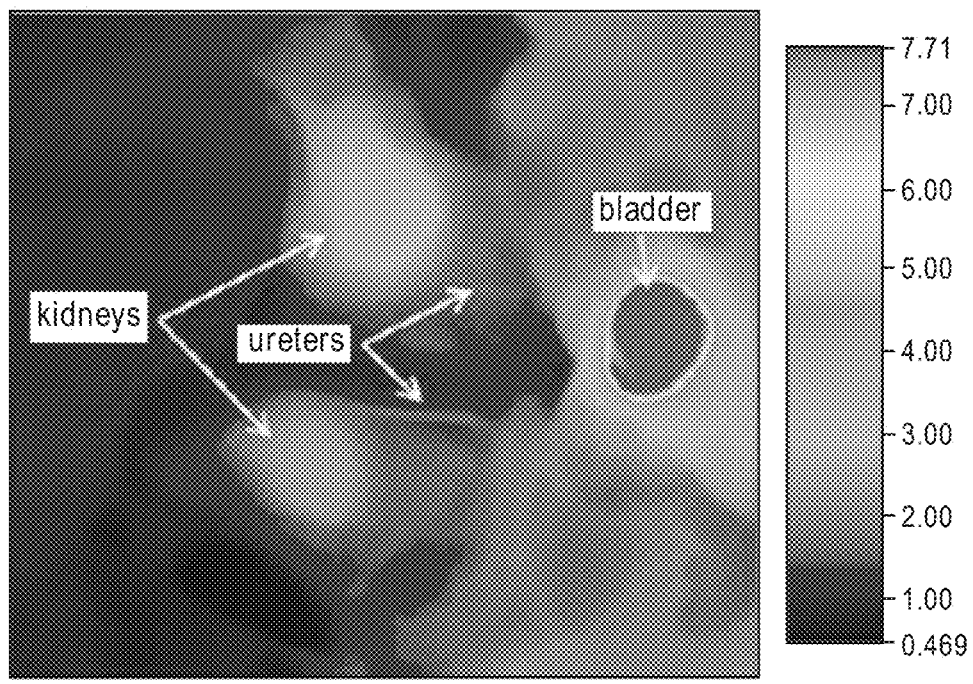
FIG. 7 illustrates image captured of ureters, kidneys and bladder in mouse after administration of the compound of Formula 1 probe.

FIG. 7 illustrates the ureters along with kidney and bladder. When the compound of Formula 1 was administered to screen the ureter of the kidney, an image of the region was captured post-administration.

Figure 8A:
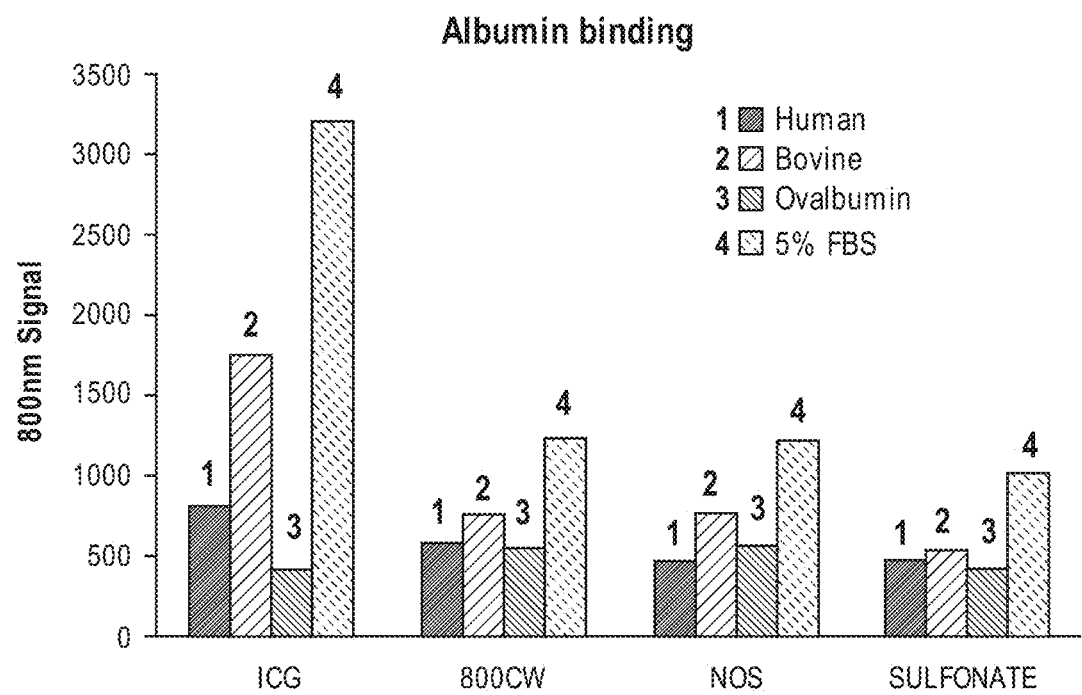
FIGS. 8A-B illustrate fluorescence detection of probes in a histogram of stained electrophoresis gels of selected proteins showing non-specific or affinity of the named dyes to human (H), bovine (B), ovalbumin (O), or 5% FBS (fetal bovine serum) (FIG. 8A). In the fluorescence images of stained electrophoresis gels dark grey represents the signal from the compound being examined, light grey represents a Coomassie Blue assessment of protein loading and white represents where both colors reside (FIG. 8B).
Figure 8B:
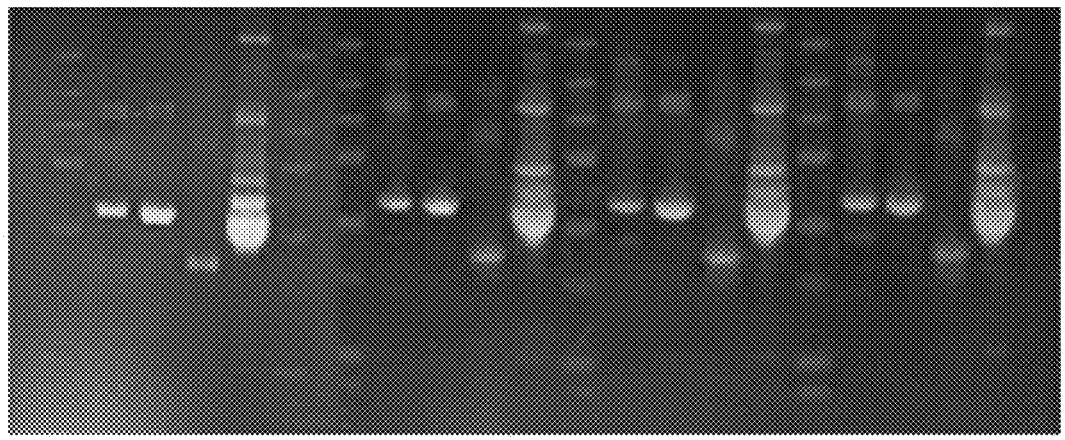

FIG. 8 illustrates fluorescence images of stained electrophoresis gels of selected proteins showing non-specific or affinity of the named compounds to human (H), bovine (B), ovalbumin (O), or 5% FBS (fetal bovine serum). It is clear that the compound of Formula 2 has potential to be useful for biliary duct examinations, similar to ICG.

Example 7: Mouse Urine

Figure 9:
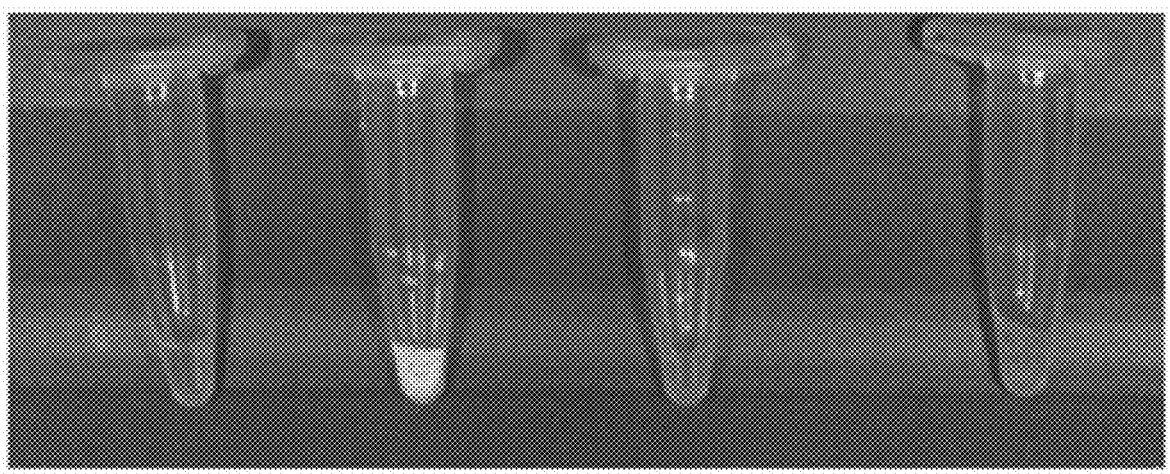
FIG. 9 illustrates fluorescent signal (800 nm) analysis of mouse urine for a control sample (no probe), the compound of Formula 1, the compound of Formula 2, and indocyanine green (ICG) dye.

With the primary elimination route being renal for the compound of Formula 1, the urine output in mice was analyzed. Urine was obtained from mice that received: neither of the compound of Formula 1 nor the compound of Formula 2 (control), the compound of Formula 1, ICG, and the compound of Formula 2. The urine was extracted with an acetonitrile:methanol mix and imaged on an Odyssey CLx imager (LI-COR Biosciences) as shown in FIG. 9.

No fluorescent signal was seen for the control and ICG. ICG is eliminated by the liver so no signal is expected. There was a slight fluorescence for the compound of Formula 2 that suggests liver excretion is not quite exclusive.

Example 8: Comparison with ICG

A comparison between the compound of Formula 2 and ICG was conducted for their common application in imaging the biliary duct (FIGS. 10A and 10B). A Pearl Impulse small animal imaging system was used for all animal and organ image acquisitions. ICG is not very soluble in aqueous media and gives a much weaker fluorescent signal than the compound of Formula 2 in vivo. A 50 nmole solution of ICG in phosphate buffer saline solution was prepared, injected intravenously, and compared for localization with a 1 nmole solution of the compound of Formula 2 at time periods of 1 min, 30 min, 2 hrs, 5 hrs, and 24 hrs.

Figure 10E:
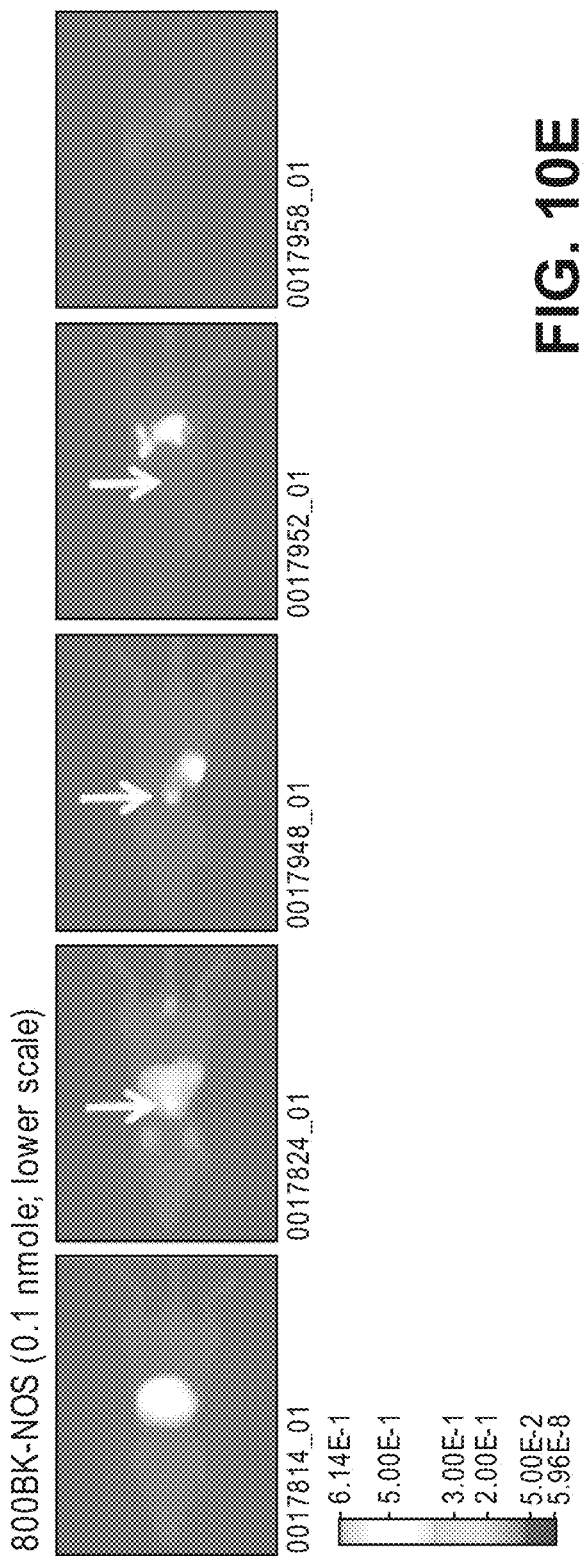

A comparison of the dose responses for the compound of Formula 2 are shown in FIG. 10B (1 nmole), FIG. 10C (0.5 nmole), and FIGS. 10D and 10E (0.1 nmole) at time periods of 1 min, 30 min, 2 hrs, 5 hrs, and 24 hrs. All images are presented using the same LUT table except FIG. 10E where the LUT for FIG. 10D has been reduced to brighten the 800 nm signal so they are visible.

The gall bladder is visible by 30 min post-intravenous administration for the 1 nmole (FIG. 10B) and 0.5 nmole (FIG. 10C) doses and continues to be visible in the 2 hrs and 5 hrs images. The images for the 0.1 nmole dose in FIG. 10D appear to show very low detection signal using the same scale as the 1 nmole and 0.5 nmole dose series. However, if the scale is adjusted as in FIG. 10E, the gall bladder target region is visible on a very low background. A wide range of dosing is possible to accommodate a particular imaging system or application.

Example 9: Excised Organ Evaluation

Fluorescent signal intensities of various organs were examined at 24 hrs and 72 hrs for the compound of Formula 1 and the compound of Formula 2 (FIG. 11A-11E). Organs examined included: heart (Ht), lungs (Ln), kidney (Kd), liver (Lv), spleen (Spl), intestine (Int), brain (Br), and muscle (Ms). At 24 hrs, there remains some signal in the liver and kidney but by 72 hrs the signal is diminished substantially.

Figure 11A:
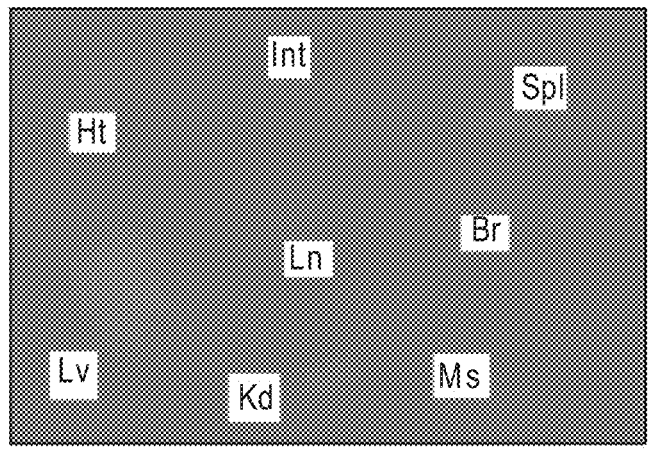
FIGS. 11A-11H show images of various mouse organs after administration. Fluorescence images of various mouse organs at 24 and 72 hrs post-administration for the comparative control (FIG. 11A), compound of Formula 1 (FIGS. 11C and 11E) and compound of Formula 2 (FIGS. 11B and 11D). Organs examined included: heart (Ht), lungs (Ln), kidney (Kd), liver (Lv), spleen (Spl), intestine (Int), brain (Br), and muscle (Ms). At 24 hrs, there remains some signal in the liver and kidney but by 72 hrs the signal is diminished substantially.

FIG. 11A shows the results using the control (800CW), 24 hours post administration.

Figure 11B:
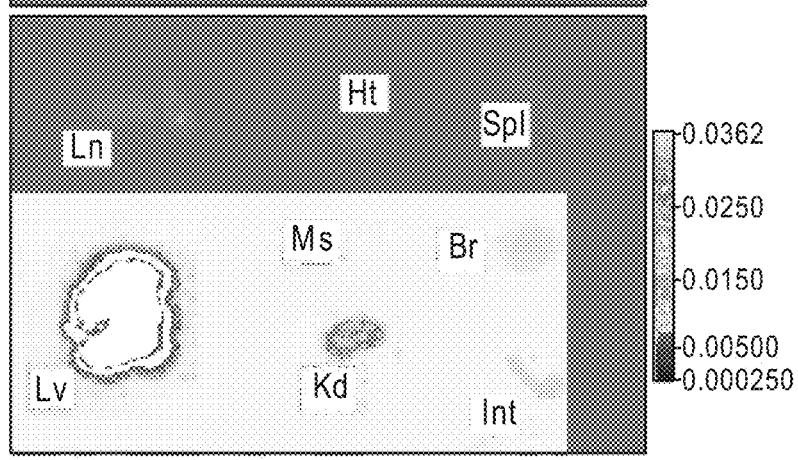
Figure 11C:
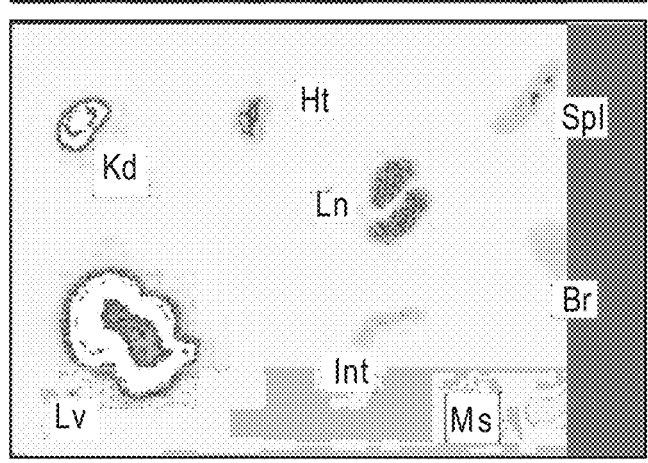

FIG. 11B shows the results using a compound of Formula 2, 24 hours post administration. FIG. 11C shows the results using a compound of Formula 1, 24 hours post administration.

Figure 11D:
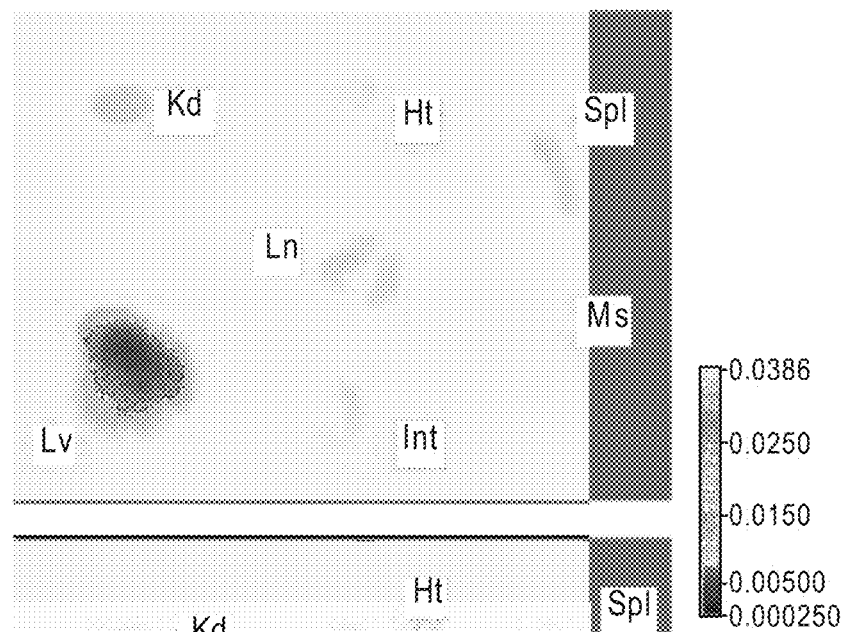
Figure 11E:
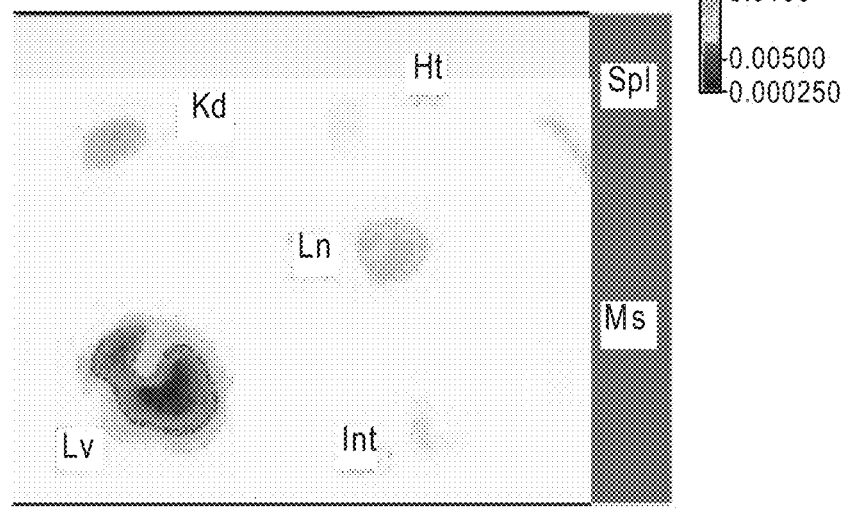

FIG. 11D-11E show the results 72 hours post administration of Formula 2 and Formula 1, respectively.

Figures 11F, 11G, 11H:
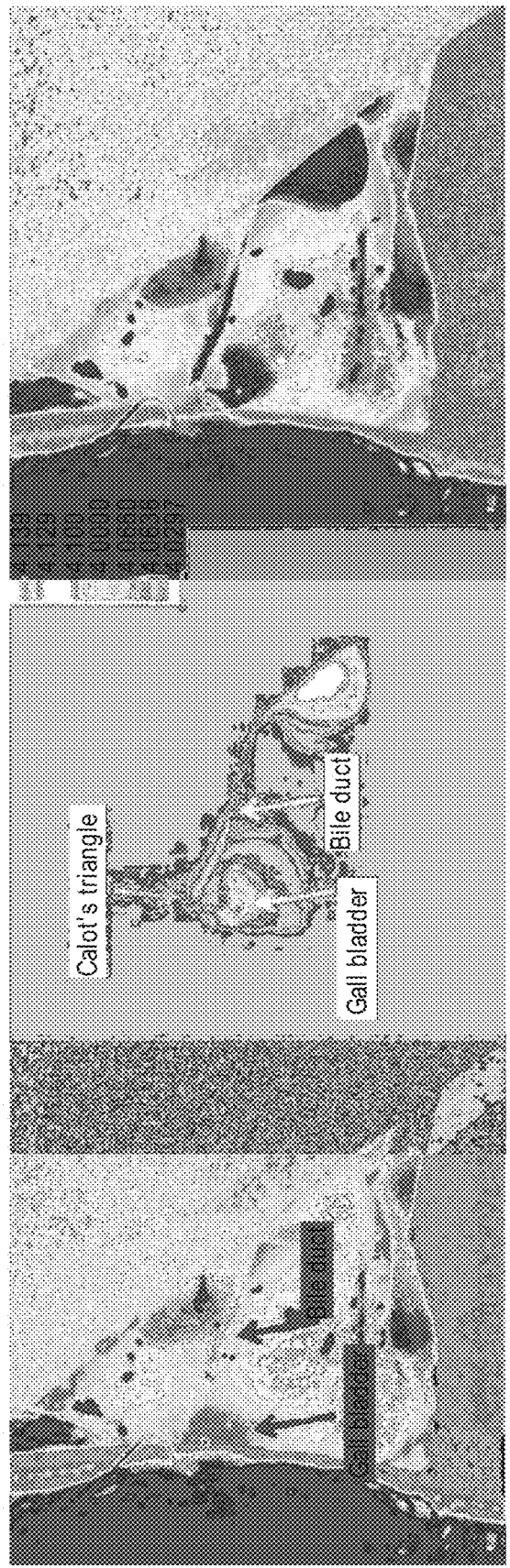

FIG. 11F shows a surgically opened animal for determining whether biliary structures are visible. The animal's liver was positioned to expose the critical structures. The image series of FIG. 11F-11H present the white light image of the liver with lobes raised to expose the gall bladder and biliary duct associated with Calot's triangle; the 800 nm image as detected by fluorescence studies of a compound of Formula 2; and a composite image overlaying the 800 nm image atop the white light image.

Example 10: Elimination Routes in Mice

Figure 12:
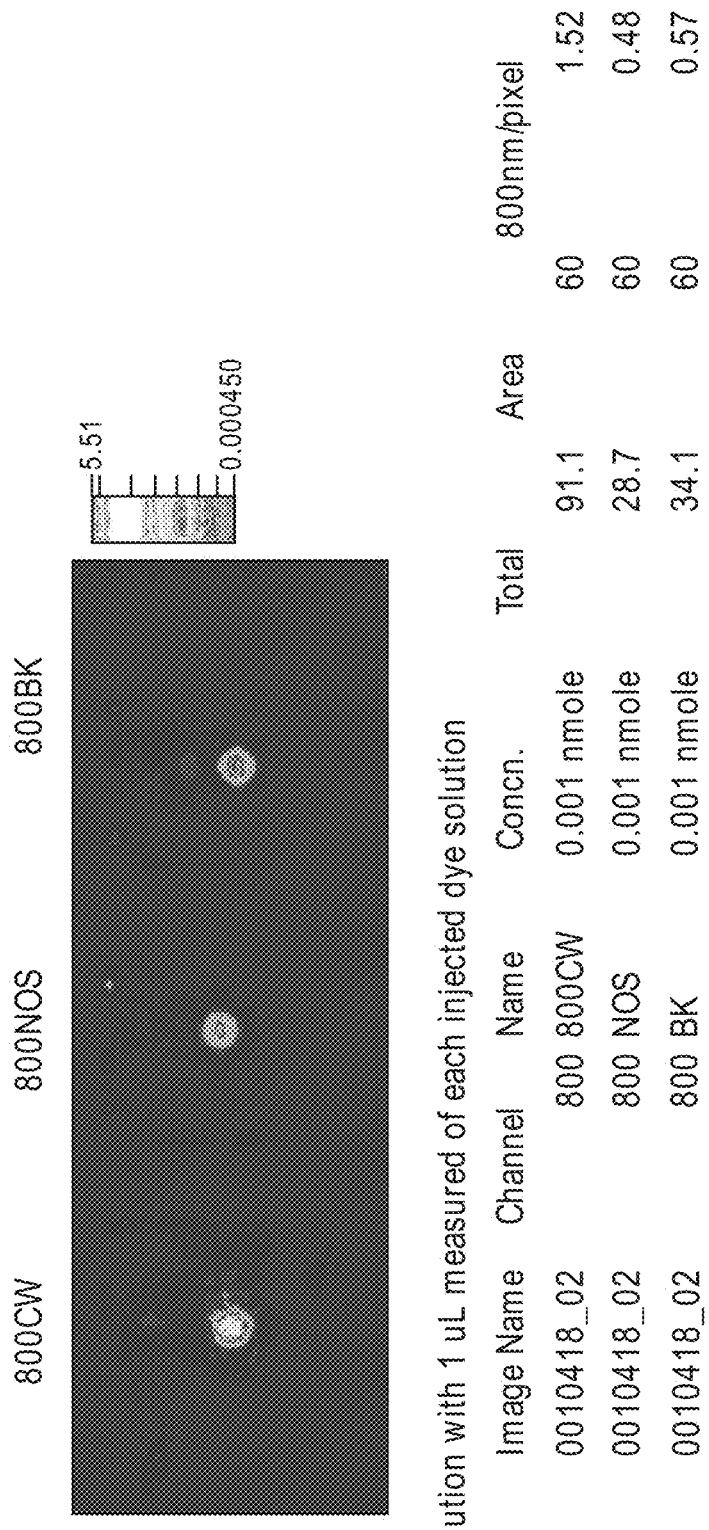
FIG. 12 shows a spot test of the injected dye solutions-800CW, 800BK-sulfonate (compound of Formula 1; 800BK or BK) and 800BK-NOS (compound of Formula 2; 800NOS or NOS).

This example describes an experiment to evaluate the excretion of the dyes described herein from animals injected with such. The dyes tested were stable cyanine dyes (IRdyes): 800CW, 800BK-sulfonate (compound of Formula 1; 800BK or BK) and 800BK-NOS (compound of Formula 2; 800NOS or NOS). In this study 12 nude mice (3 per treatment group) were injected with either (1) no probe (control group); (2) 800CW; (3) 800NOS; or (4) 800BK. The three probes (800CW-1166 g/mole (should have been 1091.1 g/mole), 800NOS-1011.09 g/mole, and 800BK-1113.14 g/mole) were dissolved in PBS. A spot test of the three probes was performed to detect the fluorescent signal when diluted to the injection dose of 1 nmole/100 µl (FIG. 12). The fluorescence of 800CW was slightly higher than that of 800NOS and 800BK.

Figure 13A:
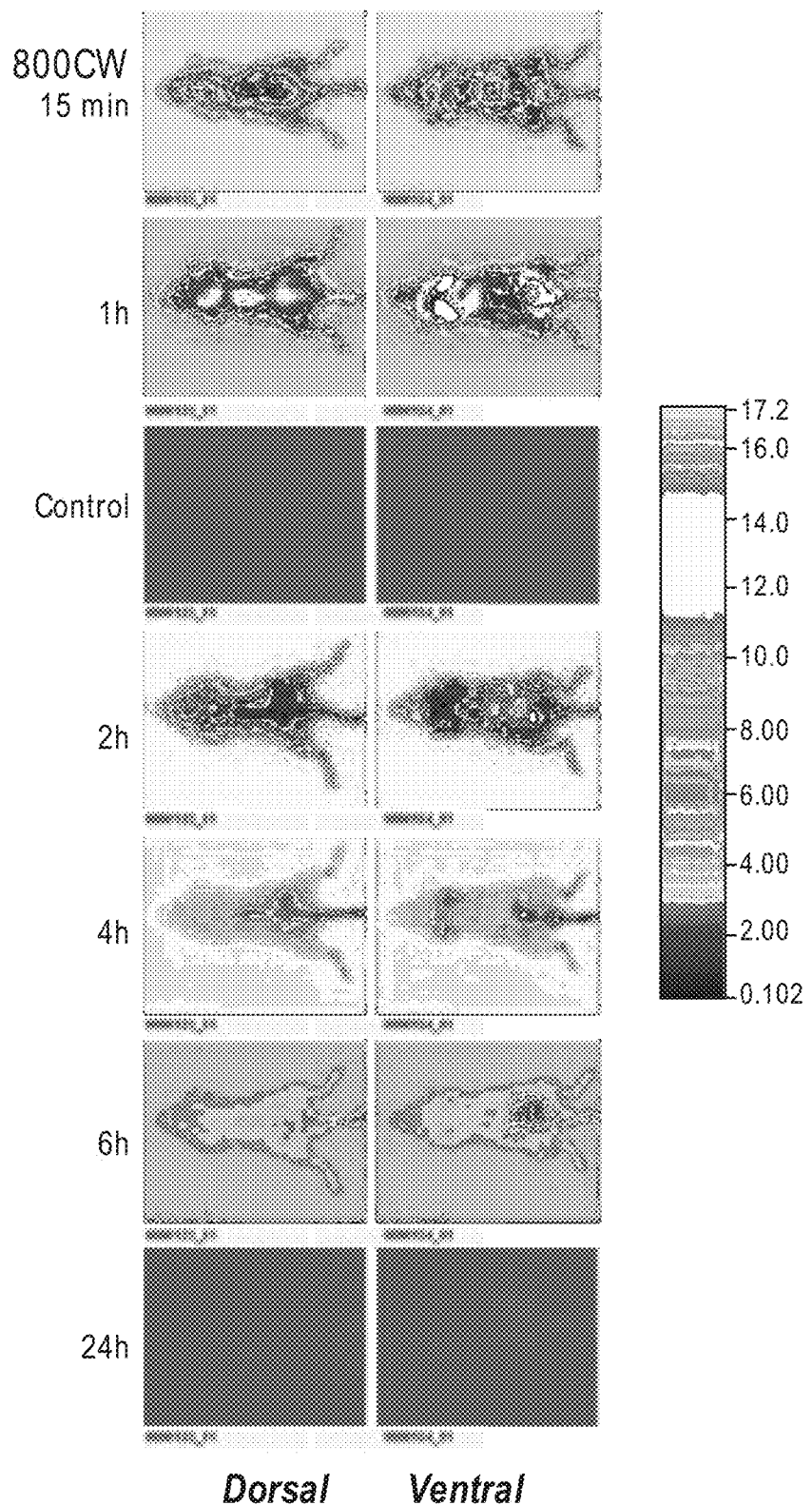
FIGS. 13A-13C show whole animal imaging of dorsal and ventral view of a representative mouse injected with one of the dyes tested. Each panel of figures shows a dorsal and ventral view of the animal at 15 minutes, 1 hour, 2 hours, 4 hours 6 hours and 24 hours after injection. An animal injected with 800CW dye, 800NOS dye, and 800BK dye are shown in FIG. 13A, FIG. 13B and FIG. 13C, respectively.
Figure 13B:
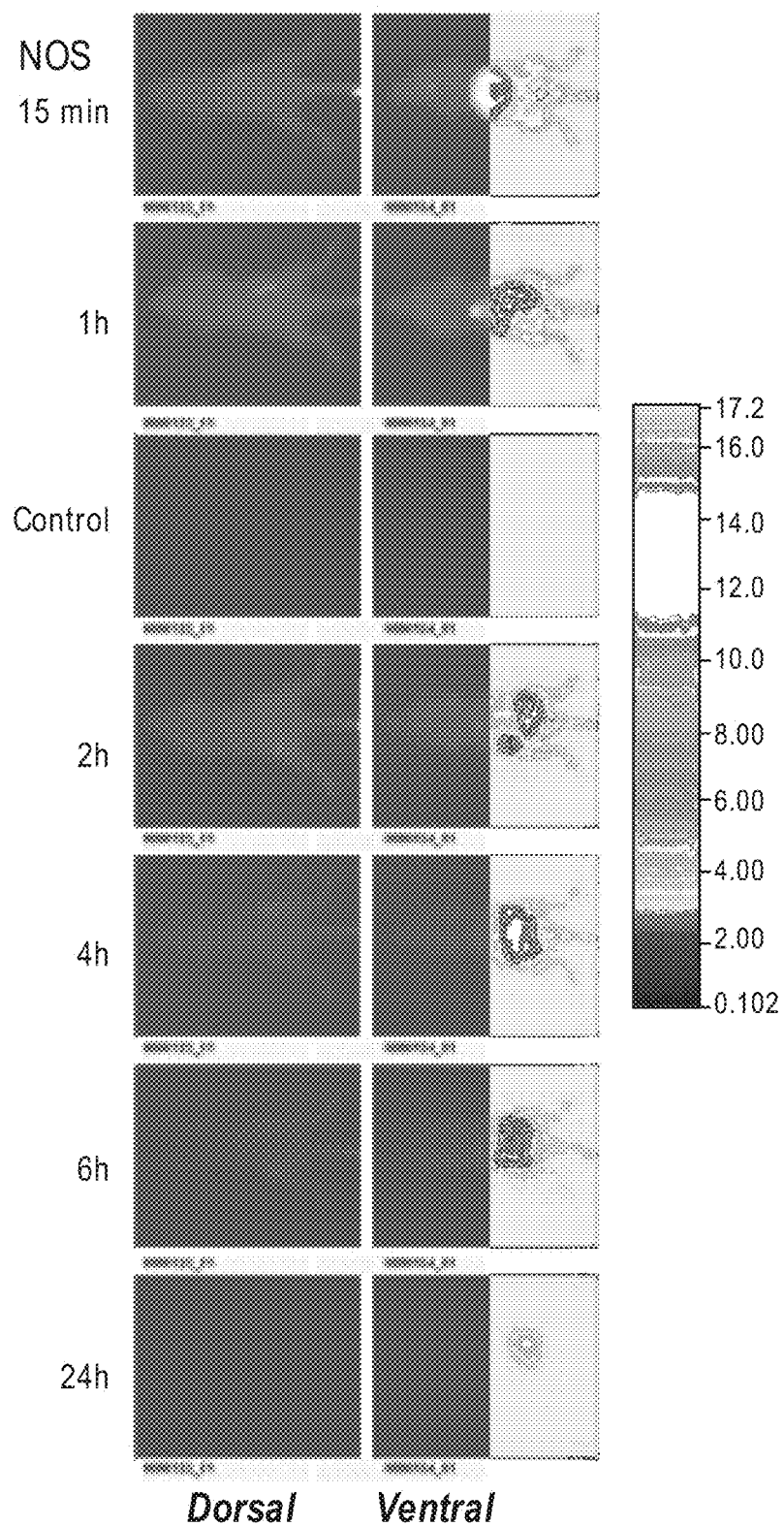
Figure 13C:
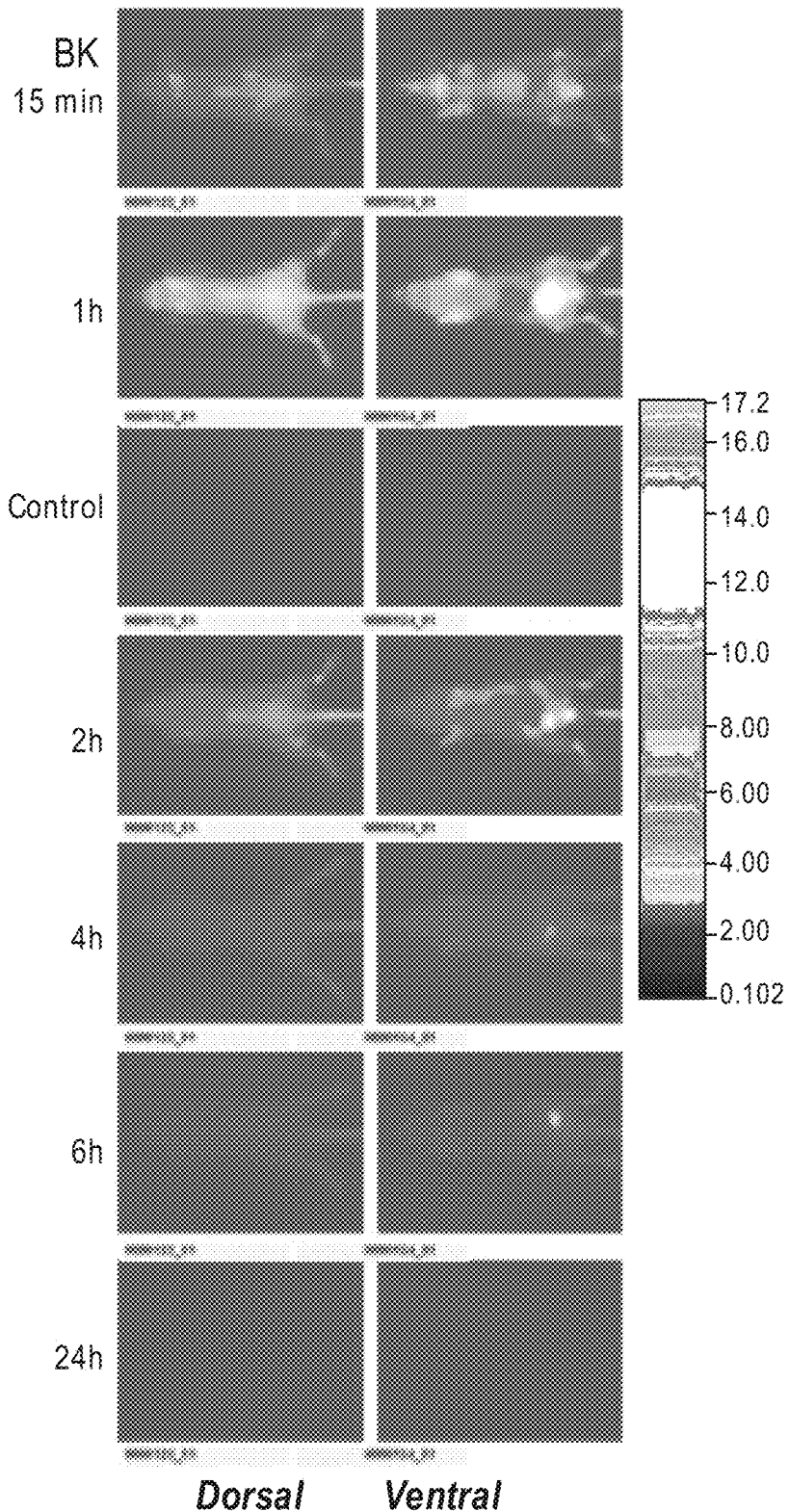

The mice received 1 nmole of dye by tail vein injection. The mice were imaged serially over 24 hours after IV injection: 5 minutes, 1 hour, 2 hours, 4 hours, 6 hours and 24 hours after injection. A representative series of images are presented in FIGS. 13A-13C of one animal per dye. All the data was normalized to the same LUT. A control mouse (no probe) was used as a reference (no signal control). Imaging was performed using the Pearl® Trilogy Imaging System (LI-COR®).

Figure 14:
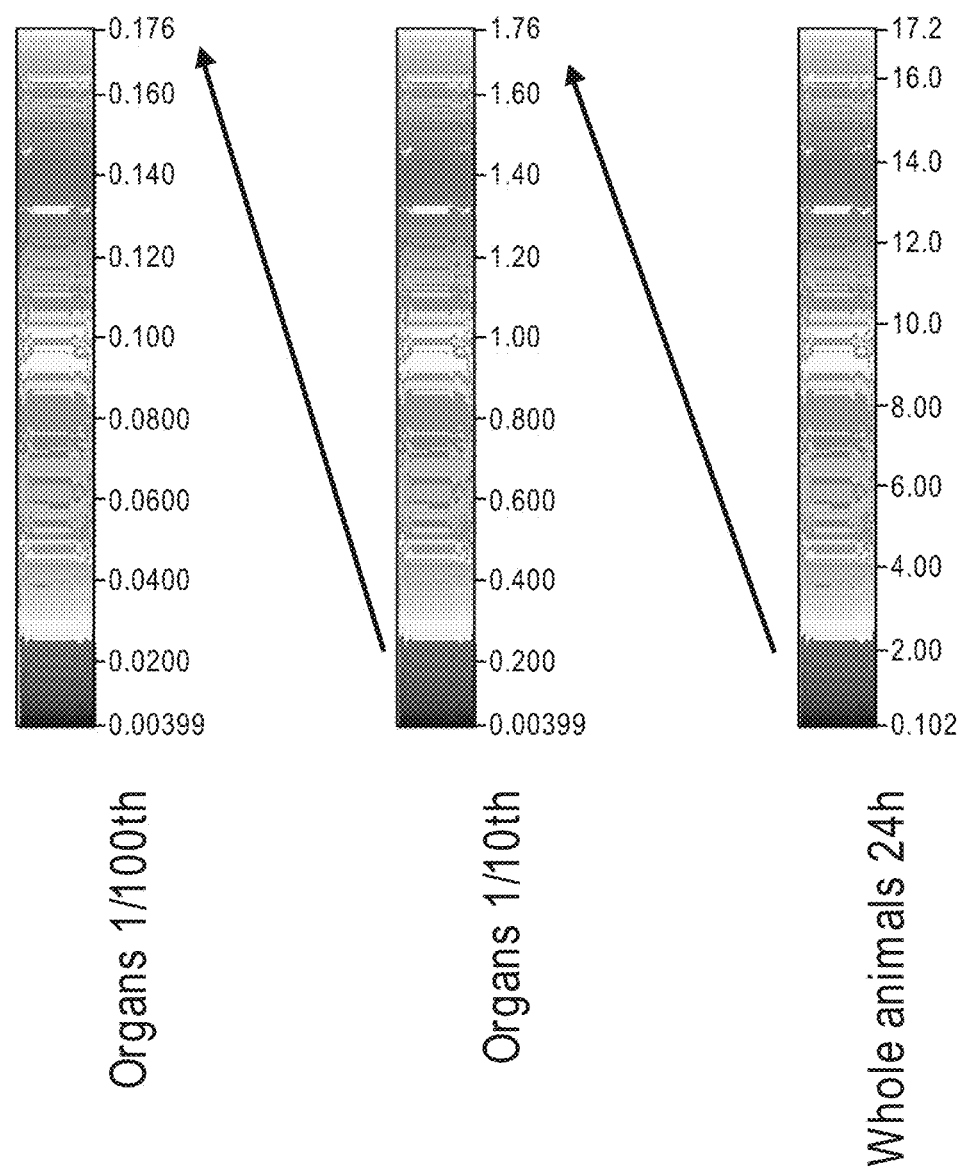
FIG. 14 shows the whole animal LUT scale, the organ $1/10^{th}$ LUT scale, and the organ $1/100^{th}$ LUT scale.

The mice were then sacrificed and their organs and tissue (i.e., liver, kidney, lungs, spleen and muscle) were harvested. The organs were imaged to detect fluorescence. When the same LUT was used for the animal and organ images, fluorescence in the organs was not detectable. As such, the low end of the animal scale was expanded such that the images of the organs could be evaluated (FIG. 14). For example, the "Organs $1/10^{th}$ scale" was used for the images of FIGS. 15A-15D and the "Organs $1/100^{th}$ scales was used for the images of FIGS. 16A-16D.

FIG. 15A shows no fluorescence in the organs of the control animal. Kidneys (lower left corner) and liver (lower right corner) had a detectable signal in the animals treated with 800CW (FIG. 15B), 800NOS (FIG. 15C), and 800BK (FIG. 15D). No muscle (top right corner) or lung tissue (top left corner) was visible in the treatments except for the 800CW treatment. At the $1/10^{th}$ LUT scale, the high level is $1/10^{th}$ that of the whole animal LUT scale. The data shows that there is only residual dye remaining in these organs when imaging at the whole animal LUT scale.

FIGS. 16A-D show some signal in the organs if the whole animal LUT scale is reduced to 100× such that the adjusted scale is $1/100^{th}$ the whole animal scale. FIG. 16A shows the signal from the control animal. FIGS. 16B, 16C and 16D shows the signal from organs of the 800CW treated animal, the 800NOS treated animal and the 800BK treated animal, respectively.

800CW and 800BK was excreted renally. The higher overall signal in the 800CW animals is mainly due to the accidentally higher concentration of the probe injected into the animals.

800NOS was eliminated from the body via the biliary tract (liver, gall bladder and bile ducts) and intestines. In the 800NOS treated animals, the liver was visible at 15 minutes and then the gall bladder, as the dye rapidly left the liver. The data also showed that the dye was moved into the intestines for excretion. The predominant signal between 2-6 hours was in the intestines. At 24 hours post injection the intestinal signal was barely detectable.

The organs were imaged under three LUT scales; each being progressively smaller in the signal range covered. The lower levels of each progressive scale were expanded to cover the full red to blue color range (FIG. 14). Very little signal remained in any of the target organs such as liver, kidney, lungs and muscle. Similar signal intensities were found in the kidney for 800CW and 800BK. In the liver, 800BK had a higher signal compared to 800CW. The results show that 800BK has a longer retention time in the liver compared to 800CW and 800NOS. This may be due to increased (higher) plasma protein binding of 800BK than 800CW.

This example shows that the clearance of IRDye 800NOS is rapid from the whole body to the biliay system with a very short retention time in the liver and also rapid excretion into the intestines. The rapid clearance by the liver implies that 800NOS has low plasma protein binding activity.

Example 11: Ureter Visualization During a Hysterectomy

The pharmaceutical formulation of Formula 1 is dissolved in a vial (25 mg) with 5 mL of saline (0.9% sodium chloride) and is administered to a patient via a bolus injection at the concentration of 5 mg/mL, 15 minutes prior to the surgery. The medical device for this procedure is the PINPOINT Endoscopic Fluorescence Imaging System (Novadaq, Mississauga, Ontario, Canada). At any point during the procedure, when the surgeon needs to identify the ureter, the device's mode is switched to the near-infrared detection imaging, and the surgeon visualizes the ureter via the monitor or display of the medical device. This identification of the ureter is visualized on the monitor as an overlay image, in which the surgeon can simultaneously locate the ureter with white light imaging.

Example 12: Biliary Duct Visualization During a Cholecystectomy

The pharmaceutical formulation of Formula 2 is dissolved in a vial (25 mg) with 5 mL of saline (0.9% sodium chloride) and is administered to a patient via a bolus injection at the concentration of 5 mg/mL, 15 minutes prior to the surgery starting. The medical device for this procedure is the da Vinci Firefly Surgical System (Intuitive Surgical, Sunnyvale Calif.). During the procedure, when the surgeon needs to identify the biliary duct, the device's mode is switched to the near-infrared detection imaging, and the surgeon identifies the biliary duct via the monitor or display of the medical device by switching between the white light image and the near-infrared image as needed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for kidney ureter imaging in a subject, the method comprising:
providing a polymorphic compound of sodium 2-((E)-2-((E)-3-(2-((E)-3,3-dimethyl-5-sulfonato-1-(4-sulfonatobutyl)indolin-2-ylidene)ethylidene)-2-(4-sulfonatophenoxy)cyclohex-1-en-1-yl)vinyl)-3,3-dimethyl-1-(4-sulfonatobutyl)-3H-indol-1-ium-5-sulfonate of Formula 1:

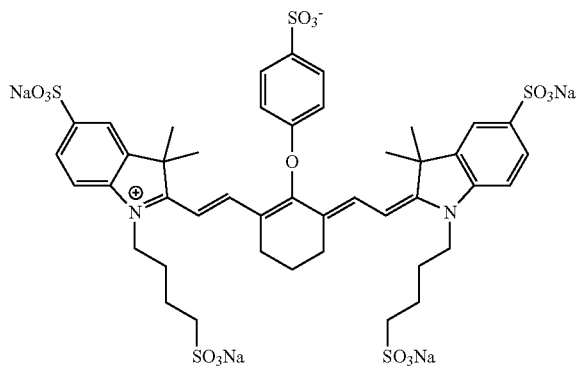

(1)

wherein the polymorph is a member selected from the group consisting of Form A having an X-ray powder diffraction pattern comprising peaks at 2-theta at 4.30±0.2°, 9.60±0.2° and 12.9°±0.2° and Form B having an X-ray powder diffraction pattern comprising peaks at 2-theta at 5.3°±0.2°, 14.2°±0.2° and 21.2°±0.2°;
admixing said polymorphic compound along with a saccharide stabilizing agent and thereafter dissolving in a pharmaceutically acceptable carrier to make a pharmaceutical composition;
administering the pharmaceutical composition to the subject;
exposing tissue of the subject's renal system to electromagnetic radiation; and
detecting fluorescence radiation from the compound.

2. The method of claim 1, wherein the polymorphic form is Form A.

3. The method of claim 1, wherein the polymorphic form is Form B.

4. The method of claim 1, wherein the saccharide stabilizing agent is a member selected from the group consisting of a monosaccharide, a disaccharide and dextran.

5. The method of claim 4, wherein the saccharide stabilizing agent is a member selected from the group consisting of glucose, galactose, xylose, glucuronic acid, trehalose, hydroxyethyl starch, mannitol, and 5% dextrose.

6. The method of claim 1, wherein the pharmaceutical carrier is selected from the group consisting of physiological sterile saline solution, sterile water solution, pyrogen-free water solution, isotonic saline solution, and phosphate buffer solution.

7. The method of claim 1, wherein the administering is conducted at a diagnostic effective amount of the compound ranging between approximately 30.0 µg/kg and approximately 3000.0 µg/kg.

8. The method of claim 1, wherein the administering is conducted at a diagnostic effective amount of the compound ranging between approximately 35.0 µg/kg and approximately 600.0 µg/kg.

9. The method of claim 1, wherein the administering is conducted at a diagnostic effective amount of the compound ranging between approximately 40.0 µg/kg and approximately 420.0 µg/kg.

10. The method of claim 1, wherein the administering is conducted at a diagnostic effective amount of the compound ranging between approximately 60.0 µg/kg and approximately 120.0 µg/kg.

11. The method of claim 1, wherein the polymorphic form and saccharide stabilizing agent are provided in a lyophilized form and reconstituted in the pharmaceutical carrier before administering to the subject.

12. The method of claim 1, wherein the administering is conducted intravenously.

13. The method of claim 1, further comprising measuring a fluorescence intensity of the administered compound remaining at the tissue of the subject's renal system at a time period after administering.

14. The method of claim 13, wherein the measured fluorescence intensity of the administered compound is higher in the kidney as compared to a measured fluorescence intensity of the administered compound in one or more of the spleen, intestine, heart, lungs, muscle, or combinations thereof approximately up to six hours after administering.

15. The method of claim 13, wherein the measured fluorescence intensity of the administered compound is background fluorescence approximately 24 hours after administering.

16. The method of claim 1, wherein the kidney ureter imaging is performed during a procedure selected from the group consisting of a laparoscopic procedure, a robotic procedure, a robotic laparoscopic procedure, and an open procedure.

17. The method of claim 13, wherein the measured fluorescence intensity of the administered compound is measured less than 5.0 hrs, 4.75 hrs, 4.50 hrs, 4.25 hrs, 4.00 hrs, 3.75 hrs, 3.50 hrs, 3.25 hrs, 3.00 hrs, 2.75 hrs, 2.50 hrs, 2.25 hrs, 2.00 hrs, 1.75 hrs, 1.50 hrs, 1.25 hrs, 1.00 hrs, 0.90 hrs, 0.80 hrs, 0.70 hrs, 0.60 hrs, 0.50 hrs, 0.40 hrs, 0.30 hrs, 0.20 hrs after administering the compound.

* * * * *